United States Patent [19]
Sivik et al.

[11] Patent Number: 6,093,691
[45] Date of Patent: *Jul. 25, 2000

[54] RINSE ADDED FABRIC SOFTENING COMPOSITIONS AND METHOD OF USE FOR THE DELIVERY OF FRAGRANCE DERIVATIVES

[75] Inventors: Mark Robert Sivik, Fairfield; John Cort Severns, West Chester; Frederick Anthony Hartman, Cincinnati; Raymond Vernon Burkes, Forest Park; Jill Bonham Costa; John Michael Gardlik, both of Cincinnati, all of Ohio

[73] Assignee: The Procter & Gamble Company, Cincinnati, Ohio

[*] Notice: This patent is subject to a terminal disclaimer.

[21] Appl. No.: 09/242,623
[22] PCT Filed: Aug. 19, 1997
[86] PCT No.: PCT/US97/14610
§ 371 Date: Feb. 19, 1999
§ 102(e) Date: Feb. 19, 1999
[87] PCT Pub. No.: WO98/07811
PCT Pub. Date: Feb. 26, 1998

Related U.S. Application Data
[60] Provisional application No. 60/024,117, Aug. 19, 1996.
[51] Int. Cl.$^7$ ............................................. C11D 3/20
[52] U.S. Cl. ..................... 510/515; 510/521; 510/522; 510/107
[58] Field of Search ............... 510/515, 521, 510/522, 527, 107

[56] References Cited

U.S. PATENT DOCUMENTS

| | | | |
|---|---|---|---|
| 3,074,892 | 1/1963 | Kulka | 252/305 |
| 3,779,932 | 12/1973 | Jaggers et al. | 252/108 |
| 3,849,326 | 11/1974 | Jaggers et al. | 252/89 |
| 3,932,520 | 1/1976 | Hoffmann | 260/594 |
| 4,524,018 | 6/1985 | Yemoto et al. | 252/522 A |
| 4,994,266 | 2/1991 | Wells | 424/76.7 |
| 5,081,111 | 1/1992 | Akimoto et al. | 525/285 |
| 5,188,753 | 2/1993 | Schmidt et al. | 252/132 |
| 5,232,612 | 8/1993 | Trinh et al. | 252/8.6 |
| 5,266,592 | 11/1993 | Grub et al. | 514/452 |
| 5,378,468 | 1/1995 | Suffis et al. | 424/401 |
| 5,506,201 | 4/1996 | McDermott et al. | 512/4 |
| 5,531,910 | 7/1996 | Severns et al. | 510/102 |
| 5,559,088 | 9/1996 | Severns et al. | 510/102 |
| 5,626,852 | 5/1997 | Suffis et al. | 424/401 |

FOREIGN PATENT DOCUMENTS

| | | | |
|---|---|---|---|
| 1923223 | 5/1969 | Germany . | |
| 2509967 | 9/1976 | Germany . | |
| 5-230496 | 9/1993 | Japan | C11B 9/00 |
| 7-179328 | 7/1995 | Japan | A61K 7/46 |
| WO 95/04809 | 2/1995 | WIPO | C11D 3/50 |
| WO 95/16660 | 6/1995 | WIPO | C07C 43/303 |
| WO 96/14827 | 5/1996 | WIPO | A61K 7/46 |

*Primary Examiner*—John R. Hardee
*Attorney, Agent, or Firm*—Richard S. Echler, Sr.; Kim Wm. Zerby; Jacobus C. Rasser

[57] ABSTRACT

The present invention relates to a fragrance delivery system for use in laundry detergent compositions which provides a long lasting "freshness" or "clean" scent to fabric. The compositions described herein deliver highly fabric substantive pro-accords to the fabric surface during laundering wherein the pro-accords release their fragrance raw materials over a period of up to two weeks. The present invention also relates a method for delivering a pleasurable scent to fabric which has a lasting freshness quality by contacting the fabric with a laundry detergent composition which comprises the fragrance-releasable pro-accords.

14 Claims, No Drawings ial, the compositions containing the potential fragrance materials are applied directly to the substrate (i.e. skin); therefore, the deposition problems resulting from dilution, rinsing, etc. are not at issue.

RINSE ADDED FABRIC SOFTENING COMPOSITIONS AND METHOD OF USE FOR THE DELIVERY OF FRAGRANCE DERIVATIVES

This application claims the priority of U.S. Provisional Application 60/024,117, filed Aug. 19, 1996.

FIELD OF THE INVENTION

The present invention relates to rinse added fabric softening compositions containing β-keto-ester pro-fragrance compounds and methods for accomplishing the delivery of such organic pro-fragrance compounds to textile articles and other surfaces rinsed with said compositions. More particularly, the invention relates to rinse added fabric softening compositions in which there is a delayed release of fragrances from surfaces rinsed in an aqueous bath in the presence of conventional fabric softening ingredients.

BACKGROUND OF THE INVENTION

Most consumers have come to expect scented laundry products and to expect that fabrics which have been laundered to also have a pleasing fragrance. It is also desired by consumers for laundered fabrics to maintain the pleasing fragrance over time. Perfume additives make laundry compositions more aesthetically pleasing to the consumer, and in some cases the perfume imparts a pleasant fragrance to fabrics treated therewith. However, the amount of perfume carry-over from an aqueous laundry bath onto fabrics is often marginal and does not last long on the fabric. Fragrance materials are often very costly and their inefficient use in rinse added fabric softener compositions and ineffective delivery to fabrics from the rinse results in a very high cost to both consumers and fabric softener manufacturers. Industry, therefore, continues to seek with urgency for more efficient and effective fragrance delivery in fabric softener products, especially for improvement in the provision of long-lasting fragrance to the rinsed fabrics.

Carrier mechanisms for perfume delivery, such as by encapsulation, have been taught in the prior art. See for example, U.S. Pat. No. 5,188,753.

U.S. Pat. No. 5,378,468, Suffis et al, issued Jan. 3, 1995 describes specific types of personal care compositions, such as deodorant sticks, comprising assertedly "body-activated" fragrances. The term apparently refers to the previously known tendency of materials such as acetals and ketals derived from fragrance alcohols to hydrolyze under acidic pH conditions thereby releasing fragrance. See, for example, U.S. Pat. No. 3,932,520, Hoffman, issued Jan. 13, 1976.

See also, Steffen Arctander, "Perfume and Flavor Chemicals", Arctander, N.J., 1969. Factors affecting substantivity of fragrance materials on fabrics are discussed in Estcher et al. JAOCS 71 p. 31–40 (1994).

The selected potential fragrance materials described by Suffis et al include particular acetals and ketals, exemplified by propylene glycol vanillin acetal. The materials exemplified apparently are rather hydrophilic short chain alcohol or diol derivatives of fragrance aldehydes and ketones that upon hydrolysis, deliver one mole of the aldehyde per mole of the potential fragrance material. The present inventors believe that short chain hydrophilic acetal and ketal materials are incompatible with acidic rinse added fabric softening compositions as described hereinafter. The Suffis et al development is designed to be incorporated with a personal care product vehicle, resulting in clear deodorant sticks and the like.

For rinse added fabric softening use, it is important that rather hydrophobic pro-fragrant compounds be used in order to enhance deposition onto surfaces in the wash solution and retention on the washed surface during rinsing. In Suffis et al, the compositions containing the potential fragrance materials are applied directly to the substrate (i.e. skin); therefore, the deposition problems resulting from dilution, rinsing, etc. are not at issue.

Esters of perfume alcohols are known in the art for providing extended delivery of fragrances in fabric softening compositions. See, for example, U.S. Pat. No. 5,531,910, Severns, issued Jul. 2, 1996. However, the manufacture of pro-fragrant esters known in the art can present costly and significant synthetic challenges. Derivitization of tertiary fragrance alcohols into simple esters is particularly difficult, often resulting in low yields and increased levels of less desirable side products. Therefore, industry continues to seek improved alternatives for generating pro-fragrances through economic and effective means.

It has now surprisingly been discovered that these problems can unexpectedly be overcome by the use of β-keto-esters as pro-fragrances. The hydrophobic β-keto-esters of the present invention demonstrate improved substantivity through the rinse. These ingredients further provide sustained gradual release of fragrance raw materials, especially fragrance raw material alcohols and ketones, from laundry items over an extended period of time. The use of β-ketoesters also provides an alternative synthetic route to derivatize fragrance raw material alcohols into pro-fragrance compounds. This method is particularly well suited to derivatization of tertiary alcohols. Tertiary alcohols can be derivatized with higher yields and improved purity via this method.

BACKGROUND ART

The following relate to the subject matter of fragrance ingredients. U.S. Pat. No. 5,626,852 Suffis et al., issued May 6, 1997; U.S. Pat. No. 5,232,612 Trinh et al., issued Aug. 3, 1996; U.S. Pat. No. 5,506,201 McDermott et al., issued Apr. 9, 1996; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; WO 95/04,809 published Feb. 16, 1995; and WO 95/16660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention meets the aforementioned needs in that it has been surprisingly discovered that fragrance raw material alcohols can be delivered onto fabric by way of rinse added fabric softening compositions from a single precursor pro-fragrance molecule having high fabric substantivity and that these pro-fragrances thereby impart a "fresh" or "clean" aesthetic residual odor benefit to the fabric. In addition to the short-term pleasurable odor benefits, the pro-fragrances according to the present invention continue to release their fragrance raw materials for as long as several weeks depending upon the structure of the pro-fragrance.

The pro-fragrances described herein comprise fragrance raw material alcohols in a stable, releasable β-ketoester form. The pro-fragrance containing rinse added fabric conditioning compositions of the present invention can comprise any number of pro-fragrances which when taken together are capable of releasing complex perfume accords which comprise fragrance raw material alcohols, ketones, etc. In addition, the pro-fragrances of the present invention are suitable for delivery of any type of fragrance "characteristic" desired by the formulator.

The first aspect of the present invention relates to rinse added fabric softening compositions which provide fabric with enhanced fragrance longevity, comprising:

a) at least about 0.01%, preferably from about 0.01% to about 15%, more preferably from about 0.1% to about 10%, most preferably from about 0.2% to about 1% by weight, of a β-ketoester having the formula:

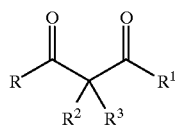

wherein R is $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, and mixtures thereof; $R^1$ is an alkoxy unit derived from a fragrance raw material alcohol; $R^2$ and $R^3$ are each independently selected from the group consisting of hydrogen, $C_1$–$C_{20}$ substituted or unsubstituted linear alkyl, $C_3$–$C_{20}$ substituted or unsubstituted branched alkyl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; and b) from about 85% to about 99.99% by weight, of ingredients useful for formulating fabric softening compositions.

The compositions of the present invention preferably comprise from about 1% to about 80%, preferably from about 5 to about 50% of cationic fabric softening compound. Dilute liquid compositions of the present invention preferably contain from about 5% to about 15% of cationic fabric softening compound. Concentrated liquid compositions of the present invention preferably contain from about 15% to about 50%, more preferably from about 15% to about 35% of cationic fabric softening compound. Preferably, the cationic fabric softening compound is selected from biodegradable quaternary ammonium compounds as described hereinafter.

The present invention also encompasses a method for contacting compositions comprising said pro-fragrant β-keto-ester as described hereinbefore with a fabric. Preferred is a method for laundering soiled fabrics, comprising contacting said fabrics with an aqueous medium containing at least about 50 ppm, preferably from about 100 ppm to about 10,000 ppm of a rinse added fabric softening composition according to the above, preferably with agitation. Said method includes the process of treating textiles in a rinse cycle of a washing machine comprising the step of contacting textiles in a washing machine with a fabric softening effective amount of a rinse added fabric softening composition comprising:

(a) from about 0.01% to about 15%, by weight of a β-ketoester pro-fragrance described herein; and (b) from about 85% to about 99.99%, by weight of the composition, of ingredients useful for formulating fabric softening compositions.

The present invention also relates to novel β-ketoester pro-fragrance materials which are suitable for use in delivering lasting fragrance benefits to fabric. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The rinse added fabric softening compositions of the present invention comprise one or more β-ketoester "pro-fragrance" compounds which are deposited onto the fabric surface during the laundry wash cycle and which are capable of releasing a fragrance raw material alcohol. The key advantages provided by the β-ketoester pro-fragrances of the present invention include chemical stability in the final product matrix, ease of formulation into the product matrix, and a highly desirable rate of fragrance raw material release. The product matrix is preferably liquid, however, granular, gelatenous, or viscous liquid embodiments are not excluded as suitable embodiments.

The β-ketoester "pro-fragrances" of the present invention begin delivering the fragrance raw material alcohols to the fabric surface as soon as the rinse added fabric softening composition is added to the laundry liquor. These "pro-fragrance" compounds are rapidly deposited onto the fabric surface due to the high fabric substantivity of the compounds and once deposited, begin to release the fragrance raw material alcohols during the remainder of the wash cycle and drying cycles. Because the β-ketoester pro-fragrances of the present invention generally have a higher molecular weight than uncombined fragrance raw material alcohols and are therefore less volatile, the pro-fragrances of the present invention are a means for effectively delivering fragrance raw material alcohols to the fabric surface even upon exposure to prolonged heating which occurs during automatic dryer usage following deposition of the compounds upon fabric during the laundry rinse cycle. Once the laundry cycle is complete, that is the clothing or fabric is dry and ready for use, the "pro-fragrance" continues to release the fragrance raw materials and because this release of material is protracted, the fabric remains smelling "fresh" and "clean" longer.

Most of the fragrance raw material alcohols and ketones which comprise the β-ketoester pro-fragrances of the present invention are not sufficiently deliverable as individual compounds to fabric via the rinse cycle either due to solubility factors (not sufficiently soluble in the laundry liquor), substantivity factors (do not sufficiently adhere to fabric surface), or volatility factors (evaporation during storage). Therefore, the pro-fragrances described herein are a means for delivering certain fragrance raw materials to fabric which could not have previously been effectively or efficiently delivered.

For the purposes of the present invention "fragrance raw materials" are herein defined as alcohols, ketones, esters, ethers, alkanes, and alkenes, especially mixed functionality compounds, for example, terpenes, having a molecular weight of at least about 100 g/mol and which are useful in imparting an odor, fragrance, essence, or scent either alone or in combination with other "fragrance raw materials".

β-Ketoester Pro-fragrances

The compositions according to the present invention comprise one or more β-ketoesters having the formula:

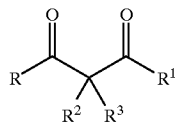

wherein R is $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, and mixtures thereof; $R^2$ and $R^3$ are each independently selected from the group consisting of hydrogen, $C_1$–$C_{20}$ substituted or unsubstituted linear alkyl, $C_3$–$C_{20}$ substituted or unsubstituted branched alkyl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof.

The β-ketoester pro-fragrances of the present invention are either "substituted" or "unsubstituted" β-ketoesters. For the purposes of the present invention the term "unsubstituted β-ketoester" is defined as "a β-ketoester pro-fragrance wherein each $R^2$ and $R^3$ is hydrogen" and "substituted β-ketoester" is defined as "a ,-ketoester pro-fragrance wherein at least one $R^2$ or $R^3$ is not a hydrogen".

For the purposes of the present invention the term "substituted" as it applies to linear alkyl, branched alkyl, cyclic alkyl, linear alkenyl, branched alkenyl, cyclic alkenyl, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_1$–$C_{12}$ branched alkoxy, preferably isopropoxy; $C_1$–$C_{12}$ cyclic alkoxy; nitrilo; halogen, preferably chloro and bromo, more preferably chloro; nitro; morpholino; cyano; carboxyl, non-limiting examples of which are —CHO; —$CO_2H$; —$CO_2^-M^+$; —$CO_2R'$; —$CONH_2$; —$CONHR^7$; —$CONR^7_2$; wherein $R^7$ is $C_1$–$C_{12}$ linear or branched alkyl); —$SO_3^-M^+$; —$OSO_3^-M^+$; —$N(R^8)_2$; and —$N^+(R^8)_3X^-$ wherein each $R^8$ is independently hydrogen or $C_1$–$C_4$ alkyl; and mixtures thereof; wherein M is hydrogen or a water soluble cation; and X is chlorine, bromine, iodine, or other water soluble anion.

For the purposes of the present invention substituted or unsubstituted aryl units are defined as phenyl moieties having the formula:

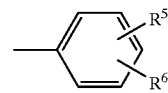

or α and β-naphthyl moieties having the formula:

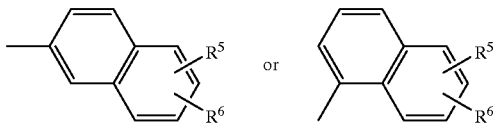

wherein $R^5$ and $R^6$ can be substituted on either ring, alone or in combination, and $R^5$ and $R^6$ are each independently hydrogen, hydroxy, $C_1$–$C_6$ alkyl, $C_2$–$C_6$ alkenyl, $C_1$–$C_4$ alkoxy, $C_1$–$C_6$ branched alkoxy, nitrilo, halogen, nitro, morpholino, cyano, carboxyl (—CHO; —$CO_2H$; —$CO_2^-M^+$, —$CO_2R^7$; —$CONH_2$; —$CONHR^7$; —$CONR^7_2$; wherein $R^7$ is $C_1$–$C_{12}$ linear or branched alkyl), —$SO_3^-M^+$, —$OSO_3^-M^+$, —$N(R^8)_2$, and —$N^+(R^8)_3X^-$ wherein each $R^8$ is independently hydrogen or $C_1$–$C_4$ alkyl; and mixtures thereof. $R^5$ and $R^6$ are preferably hydrogen $C_1$–$C_6$ alkyl, —$CO_2^-M^+$, —$SO_3^-M^+$, —$OSO_3^-M^+$, and mixtures thereof, more preferably $R^5$ or $R^6$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like.

For the purposes of the present invention substituted or unsubstituted alkylenearyl units are defined as alkylenephenyl moieties having the formula:

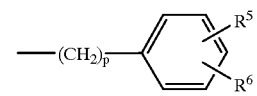

or alkylenenaphthyl moieties having the formula:

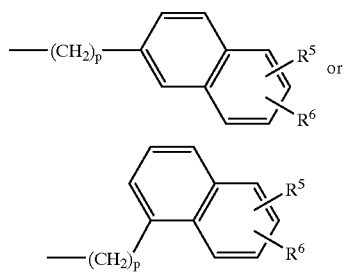

wherein $R^5$ and $R^6$ can be substituted on either ring, alone or in combination, and $R^5$ and $R^6$ are each independently hydrogen, hydroxy, $C_1$–$C_6$ alkyl, $C_2$–$C_6$ alkenyl, $C_1$–$C_4$ alkoxy, $C_1$–$C_6$ branched alkoxy, nitrilo, halogen, nitro, morpholino, cyano, carboxyl (—CHO; —$CO_2H$; —$CO_2^-M^+$, —$CO_2R^7$; —$CONH_2$; —$CONHR^7$; —$CONR^7_2$; wherein $R^7$ is $C_1$–$C_{12}$ linear or branched alkyl), —$SO_3^-M^+$, —$OSO_3^-M^+$, —$N(R^8)_2$, and —$N+(R^8)_3X^-$ wherein each $R^8$ is independently hydrogen or $C_1$–$C_4$ alkyl; and mixtures thereof; and mixtures thereof, p is from 1 to about 24. $R^5$ and $R^6$ are preferably hydrogen $C_1$–$C_6$ alkyl, —$CO_2^-M^+$, —$SO_3^-M^+$, —$OSO_3^-M^+$, and mixtures thereof, more preferably $R^5$ or $R^6$ is hydrogen and the other moiety is $C_1-C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like.

For the purposes of the present invention substituted or unsubstituted alkyleneoxy units are defined as moieties having the formula:

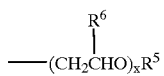

wherein $R^5$ is hydrogen; $R^6$ is hydrogen, methyl, ethyl, and mixtures thereof; the index x is from 1 to about 10.

For the purposes of the present invention substituted or unsubstituted alkyleneoxyalkyl are defined as moieties having the formula:

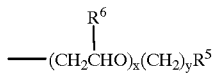

wherein $R^5$ is hydrogen, $C_1-C_{18}$ alkyl, $C_1-C_4$ alkoxy, and mixtures thereof; $R^6$ is hydrogen, methyl, ethyl, and mixtures thereof; the index x is from 1 to about 9 and the index y is from 2 to about 18.

For the purposes of the present invention substituted or unsubstituted alkyleneoxyaryl units are defined as moieties having the formula:

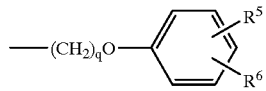

wherein $R^5$ and $R^6$ can be substituted on either ring, alone or in combination, and $R^5$ and $R^6$ are each independently hydrogen, hydroxy, $C_1-C_6$ alkyl, $C_2-C_6$ alkenyl, $C_1-C_4$ alkoxy, $C_1-C_6$ branched alkoxy, nitrilo, halogen, nitro, morpholino, cyano, carboxyl (—CHO; —$CO_2H$; —$CO_2^-M^+$, —$CO_2R'$; —$CONH_2$; —$CONHR^7$; —$CONR^7_2$; wherein $R^7$ is $C_1-C_{12}$ linear or branched alkyl), —$SO_3^-M^+$, —$OSO_3^-M^+$, —$N(R^8)_2$, and —$N+(R^8)_3X^-$ wherein each $R^8$ is independently hydrogen or $C_1-C_4$ alkyl; and mixtures thereof; and mixtures thereof, p is from 1 to about 24. $R^5$ and $R^6$ are preferably hydrogen $C_1-C_6$ alkyl, —$CO_2^-M^+$, -$SO_3^-M^+$, —$OSO_3^-M^+$, and mixtures thereof, more preferably $R^5$ or $R^6$ is hydrogen and the other moiety is $C_1-C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like.

R units are $C_1-C_{30}$ substituted or unsubstituted linear alkyl, $C_3-C_{30}$ substituted or unsubstituted branched alkyl, $C_3-C_{30}$ substituted or unsubstituted cyclic alkyl, $C_2-C_{30}$ substituted or unsubstituted linear alkenyl, $C_3-C_{30}$ substituted or unsubstituted branched alkenyl, $C_3-C_{30}$ substituted or unsubstituted cyclic alkenyl, $C_2-C_{30}$ substituted or unsubstituted linear alkynyl, $C_3-C_{30}$ substituted or unsubstituted branched alkynyl, $C_6-C_{30}$ substituted or unsubstituted alkylenearyl, $C_6-C_{30}$ substituted or unsubstituted aryl, and mixtures thereof. For the purposes of the present invention the term "substituted" as it applies to R units is the same as defined herein above.

$R^1$ is an alkoxy unit derived from a fragrance raw material alcohol. Non-limiting examples of preferred fragrance raw material alcohols include 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), α,α-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)ethanol, 3,3-dimethyl-Δ²-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, 1-phenylpropanol, 3-phenylpropanol, 2-phenylpropanol (Hydrotropic Alcohol), 2-(cyclododecyl) propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), (α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3 -hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, 5-(2, 2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbomyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl)cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1]hept-2-ene (myrtenol), 4-methyl-2,4-heptadien-1-ol, 3,4,5, 6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1 ]heptan-2-ol, 2,6-dimethylheptan-2-ol (dimetol), 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyloctahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1 H-inden-5-ol, 2-methyl-2-vinyl-5-(1-hydroxy-1-methylethyl)tetrahydrofuran, β-caryophyllene alcohol, vanillin, vanillin esters, and mixtures thereof. A listing of common fragrance raw material alcohols can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) all of which are incorporated herein by reference.

According to the present invention all isomers of a fragrance raw material whether in the form of the pro-fragrance or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R-(+)-β-citronellol and S-(−)-p-citronellol. Each of these materials separately or as a racemic pair are suitable for use as fragrance raw materials in the present invention. However, those skilled in the art of fragrances, by utilization of the present invention, should not disregard the olfactory differences that individual optical isomers, admixtures of optical isomers or admixtures of positional isomers impart. By way of example, carvone, 2-methyl-5-(1-methylethenyl)-2-cyclohexene-1-one exists as two isomers; d-carvone and l-carvone. d-Carvone is found in oil of caraway and renders a completely different fragrance from l-carvone which is found in spearmint oil. According to the present invention a pro-fragrance which releases d-carvone will result in a different scent or fragrance than one which releases l-carvone. The same applies to l-carvone. In addition, admixtures of cis/trans isomers, for example, nerol (3,7-dimethyl-cis-2,6-octadien-1-ol) and geraniol (3,7-dimethyl-trans-2,6-octadien-1-ol), are well known to those skilled in the art of perfumery. However, as in the example of geraniol and nerol, the relative amounts of these two isomers in the admixture is important when formulating fragrances or perfumes and these ratios must be taken into account and adjusted by the formulator.

More preferably, the fragrance raw material alcohol is selected from the group consisting of cis-3-hexen-1-ol, hawthanol [admixture of 2-(o-methylphenyl)-ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(l-methylethyl)cyclohexane methanol, 3-(hydroxy-methyl)-2-nonanone, octan-1-ol, 3-phenylpropanol, 3,7,11,15-tetramethylhexadec-2-en-1-ol (phytol), Rhodinal 70 [3,7-dimethyl-7-octenol, 3,7-dimethyl-6-octenol admixture], 9-decen-1-ol, α-3,3-trimethyl-2-norborane methanol, 3-cyclohexylpropan-1-ol, 3,7-dimethyl-1,6-octadien-3-ol (linalool), 4-methyl-1-phenyl-2-pentanol, 3,6-dimethyl-3-vinyl-5-hepten-2-ol, phenyl ethyl methanol; propyl benzyl methanol, 1-methyl-4-isopropenylcyclohexan-3-ol, 4-isopropyl-1-methylcyclohexan-3-ol (menthol), 4-tert-butylcyclohexanol, 2-tert-butyl-4-methylcyclohexanol, 4-isopropylcyclohexanol, trans-decahydro-β-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy-4-(1-propenyl)phenol, vanillin, vanillin esters, and mixtures thereof.

Non-limiting examples of ketones which are releasable components of the β-ketoester pro-fragrances of the present invention include but are not limited to α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, γ-methyl ionone, α-iso-methyl ionone, 4-(3,4-methylenedioxyphenyl)butan-2-one, 4-(4-hydroxyphenyl)butan-2-one, methyl β-naphthyl ketone, methyl cedryl ketone, 6-acetyl-1,1,2,4,4,7-hexamethyltetralin (tonalid), l-carvone, 5-cyclohexadecen-1-one, acetophenone, decatone, 2-[2-(4-methyl-3-cyclohexenyl-1-yl)propyl]cyclopentan-2-one, 2-sec-butylcyclohexanone, β-dihydro ionone, allyl ionone, α-irone, α-cetone, α-irisone, acetanisole, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, ethyl amyl ketone, ethyl pentyl ketone, menthone, methyl-7,3-dihydro-2H-1,5-benzodioxepine-3- one, fenchone, methyl naphthyl ketone, propyl naphthyl ketone, methyl hydroxynaphthyl ketone, and mixtures thereof.

More preferably the ketones which are released by the β-ketoesters of the present invention are α-damascone, β-damascone, δ-damascone, β-damascenone, muscone, 6,7-dihydro-1,1,2,3,3-pentamethyl-4(5H)-indanone (cashmeran), cis-jasmone, dihydrojasmone, α-ionone, β-ionone, dihydro-β-ionone, γ-methyl ionone, α-iso-methyl ionone, 4-(3,4-methylenedioxyphenyl)butan-2-one, 4-(4-hydroxyphenyl)-butan-2-one, methyl β-naphthyl ketone, methyl cedryl ketone, 6-acetyl-1,1,2,4,4,7-hexamethyltetralin (tonalid), l-carvone, 5-cyclohexadecen-1-one, methyl naphthyl ketone, and mixtures thereof.

Non-limiting examples of preferred β-ketoester pro-fragrances include 3,7-dimethyl-1,6-octadien-3-yl 3-(β-naphthyl)-3-oxo-propionate, [linalyl (2-naphthoyl)acetate], having the formula:

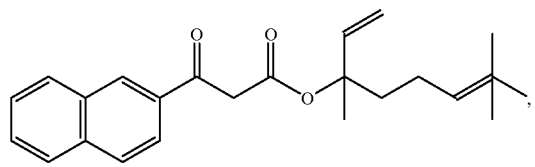

3,7-dimethyl-1,6-octadien-3-yl 3-(α-naphthyl)-3-oxo-propionate, [linalyl (1-naphthoyl)acetate], having the formula:

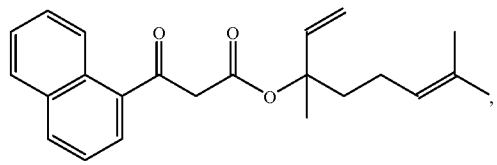

2,6-dimethyl-7-octen-2-yl 3-(4-methoxyphenyl)-3-oxo-propionate, [3-(4-methoxyphenyl)-3-oxo-propionic acid dihydromyrcenyl ester], having the formula:

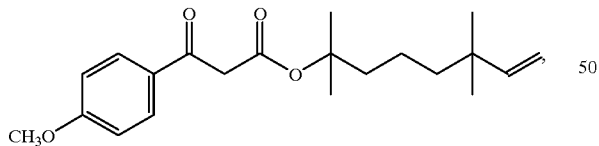

2,6-dimethyl-7-octen-2-yl 3-(4-nitrophenyl)-3-oxo-propionate, [3-(4-nitrophenyl)-3-oxo-propionic acid dihydromyrcenyl ester], having the formula:

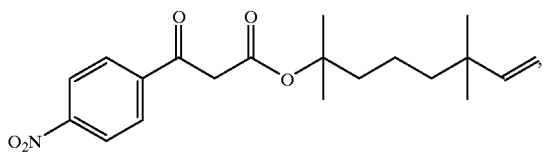

2,6-dimethyl-7-octen-2-yl 3-(β-naphthyl)-3-oxo-propionate, [dihydromyrcenyl (2-naphthoyl)acetate], having the formula:

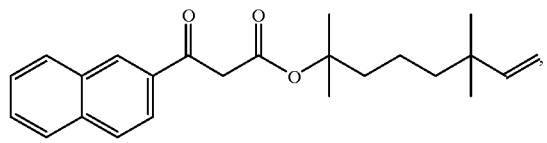

3,7-dimethyl-1,6-octadien-3-yl 3-(4-methoxyphenyl)-3-oxo-propionate, [3-(4-methoxyphenyl)-3-oxo-propionic acid linalyl ester], having the formula:

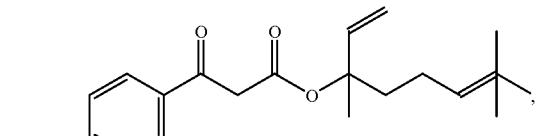

(α,α-4-trimethyl-3-cyclohexenyl)methyl 3-(β-naphthyl)-3-oxo-propionate, [α-terpinyl (2-naphthoyl)acetate], having the formula:

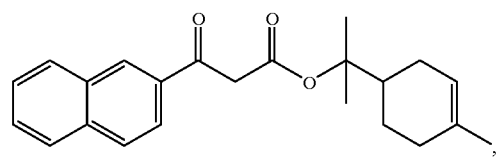

9-decen-1-yl 3-(β-naphthyl)-3-oxo-propionate, [9-decen-1-yl (2-naphthoyl)acetate], known alternatively as, roslava 2'-acetonaphthone, having the formula:

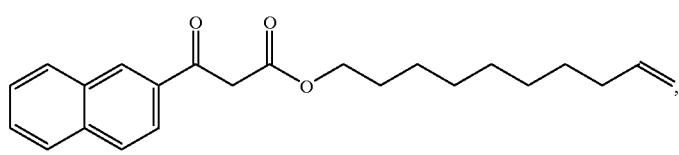

3,7-dimethyl-1,6-octadien-3-yl 3-(nonanyl)-3-oxo-propionate, [linalyl (nonanoyl)acetate], known alternatively as, octyl [(linalyl) α-acetyl] ketone, having the formula:

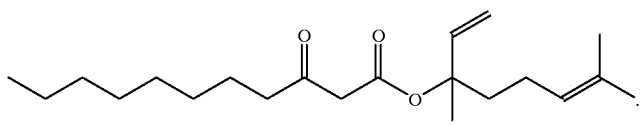

Further examples of preferred β-ketoester pro-fragrances include 3,7-dimethyl-1,6-octadien-3-yl 3-oxo-butyrate, 2,6-dimethyl-7-octen-2-yl 3-oxo-butyrate, 6-heptyl-5-hepten-2-yl 3-oxo-butyrate, 1-(prop-2-enyl)cyclopentanyl 3-oxo-butyrate, (α,α-4-trimethyl-3-cyclohexenyl)methyl 3-oxo-butyrate, cis-3-hexenyl 3-oxo-butyrate, and mixtures thereof.

The β-ketoester pro-fragrances of the present invention are capable of releasing a fragrance raw material alcohol and a fragrance raw material ketone depending upon the choice of R and $R^1$ moieties by the formulator. An example of a released ketone which is not a fragrance raw material ketone is in the case of R equal to methyl and $R^2$ and $R^3$ both equal to hydrogen. In this case the released ketone is acetone which is not a fragrance raw material as defined herein above.

Depending upon the selection of the R, $R^2$, and $R^3$ unit, the substantivity of the β-ketoester pro-fragrance can be suitably adjusted by the formulator to provide more or less deposition onto fabric. Those skilled in the art of formulating detergent compositions will recognize that the terms "substantive" and "substantivity" refer to the propensity of a compound to adhere to, associate with, or deposit upon a surface, preferably the surface of fabric. Therefore, compounds which are more substantive more readily adhere to fabric surface. However, substantive compounds, in general, do not react with the surface onto which they deposit.

As described hereinabove, it has been surprisingly discovered that pro-fragrances of the present invention, when applied to fabric, break down thereby releasing an alcohol and a ketone. For example, the pro-fragrance 3,7-dimethyl-1,6-octadien-3-yl 3-(β-naphthyl)-3-oxo-propionate having the formula:

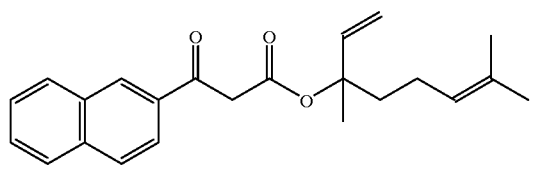

breaks down to release the fragrance raw material alcohol linalool having the formula:

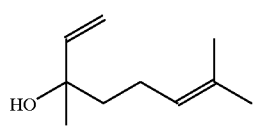

and the fragrance raw material ketone methyl naphthyl ketone having the formula:

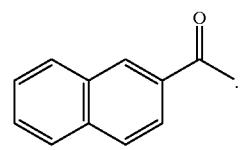

A further example includes 2,6-dimethyl-7-octen-2-yl 3-(4-methoxyphenyl)-3-oxo-propionate having the formula:

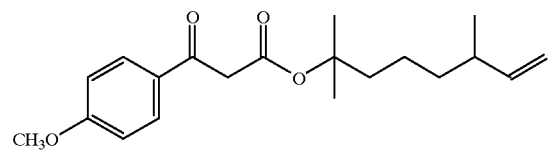

which breaks down to release the fragrance raw material alcohol dihydromyrcenol having the formula:

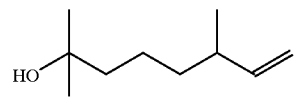

and methyl 4-methoxyphenyl ketone having the formula:

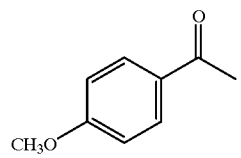

Fabric Softening Ingredients

The preferred fabric softening agents which comprise the rinse added fabric softening compositions of the present invention have the formula:

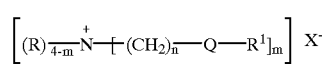

or the formula:

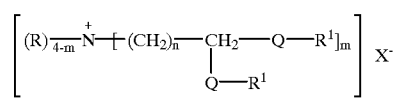

wherein Q is a carbonyl unit having the formula:

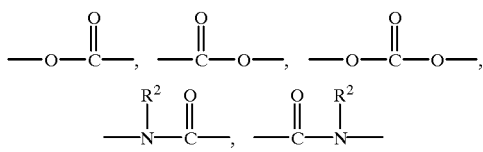

each R unit is independently hydrogen, $C_1$–$C_6$ alkyl, $C_1$–$C_6$ hydroxyalkyl, and mixtures thereof, preferably methyl or hydroxy alkyl; each $R^1$ unit is independently linear or branched $C_{11}$–$C_{22}$ alkyl, linear or branched $C_{11}$–$C_{22}$ alkenyl, and mixtures thereof, $R^2$ is hydrogen, $C_1$–$C_4$ alkyl, $C_1$–$C_4$ hydroxyalkyl, and mixtures thereof; X is a cation which is compatible with fabric softener actives and adjunct ingredients; the index m is from 1 to 4; the index n is from 1 to 4.

An example of a preferred fabric softener active is a mixture of quaternized amines having the formula:

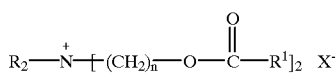

wherein R is preferably methyl; $R^1$ is a linear or branched alkyl or alkenyl chain comprising at least 11 atoms, preferably at least 15 atoms. In the above fabric softener example, the unit —$O_2CR^1$ represents a fatty acyl unit which is typically derived from a triglyceride source. The triglyceride source is preferably derived from tallow, partially hydrogenated tallow, lard, partially hydrogenated lard, vegetable oils and/or partially hydrogenated vegetable oils, such as, canola oil, safflower oil, peanut oil, sunflower oil, corn oil, soybean oil, tall oil, rice bran oil, etc. and mixtures of these oils.

The preferred fabric softening actives of the present invention are the Diester and/or Diamide Quaternary Ammonium (DEQA) compounds, the diesters and diamides having the formula:

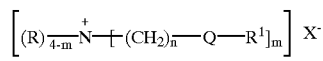

wherein R, $R^1$, X, and n are the same as defined herein above and Q has the formula:

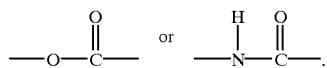

These preferred fabric softening actives are formed from the reaction of an amine with a fatty acyl unit to form an amine intermediate having the formula:

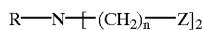

wherein R is preferably methyl, Z is —OH, —$NH_2$, or mixtures thereof; followed by quaternization to the final softener active.

Non-limiting examples of preferred amines which are used to form the DEQA fabric softening actives according to the present invention include methyl bis(2-hydroxyethyl) amine having the formula:

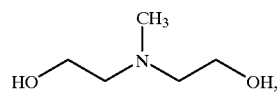

methyl bis(2-hydroxypropyl)amine having the formula:

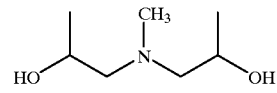

methyl (3-aminopropyl) (2-hydroxyethyl)amine having the formula:

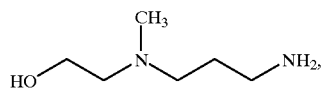

methyl bis(2-aminoethyl)amine having the formula:

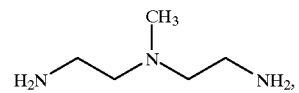

triethanol amine having the formula:

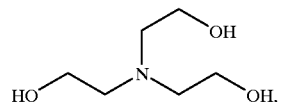

di(2-aminoethyl) ethanolamine having the formula:

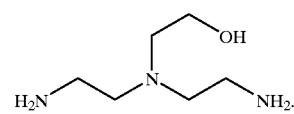

The counterion, $X^{(-)}$ above, can be any softener-compatible anion, preferably the anion of a strong acid, for example, chloride, bromide, methylsulfate, ethylsulfate, sulfate, nitrate and the like, more preferably chloride. The anion can also, but less preferably, carry a double charge in which case $X^{(-)}$ represents half a group.

Tallow and canola are convenient and inexpensive sources of fatty acyl units which are suitable for use in the present invention as $R^1$ units. The following are non-limiting examples of quaternary ammonium compounds suitable for use in the compositions of the present invention. The term "tallowyl" as used herein below indicates the $R^1$ unit is derived from a tallow triglyceride source and is a mixture of fatty acyl units. Likewise, the use of the term canolyl refers to a mixture of fatty acyl units derived from canola oil.

Table II
Fabric Softener Actives

N,N-di(tallowyl-oxy-ethyl)-N,N-dimethyl ammonium chloride;

N,N-di(canolyl-oxy-ethyl)-N,N-dimethyl ammonium chloride;

N,N-di(tallowyl-oxy-ethyl)-N-methyl, N-(2-hydroxyethyl) ammonium chloride;

N,N-di(canolyl-oxy-ethyl)-N-methyl, N-(2-hydroxyethyl) ammonium chloride;

N,N-di(2-tallowyloxy-2-oxo-ethyl)-N,N-dimethyl ammonium chloride;

N,N-di(2-canolyloxy-2-oxo-ethyl)-N,N-dimethyl ammonium chloride

N,N-di(2-tallowyloxyethylcarbonyloxyethyl)-N,N-dimethyl ammonium chloride;

N,N-di(2-canolyloxyethylcarbonyloxyethyl)-N,N-dimethyl ammonium chloride;

N-(2-tallowoyloxy-2-ethyl)-N-(2-tallowyloxy-2-oxo-ethyl)-N,N-dimethyl ammonium chloride;

N-(2-canolyloxy-2-ethyl)-N-(2-canolyloxy-2-oxo-ethyl)-N,N-dimethyl ammonium chloride;

N,N,N-tri(tallowyl-oxy-ethyl)-N-methyl ammonium chloride;

N,N,N-tricanolyl-oxy-ethyl)-N-methyl ammonium chloride;

N-(2-tallowyloxy-2-oxoethyl)-N-(tallowyl)-N,N-dimethyl ammonium chloride;

N-(2-canolyloxy-2-oxoethyl)-N-(canolyl)-N,N-dimethyl ammonium chloride;

1,2-ditallowyloxy-3-N,N,N-trimethylammoniopropane chloride; and 1,2-dicanolyloxy-3-N,N,N-trimethylammoniopropane chloride;

and mixtures of the above actives.

Particularly preferred is N,N-di(tallowoyl-oxy-ethyl)-N,N-dimethyl ammonium chloride, where the tallow chains are at least partially unsaturated.

The level of unsaturation contained within the tallow, canola, or other fatty acyl unit chain can be measured by the Iodine Value (IV) of the corresponding fatty acid, which in the present case should preferably be in the range of from 5 to 100 with two categories of compounds being distinguished, having a IV below or above 25.

Indeed, for compounds having the formula:

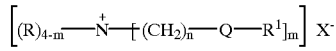

derived from tallow fatty acids, when the Iodine Value is from 5 to 25, preferably 15 to 20, it has been found that a cis/trans isomer weight ratio greater than about 30/70, preferably greater than about 50/50 and more preferably greater than about 70/30 provides optimal concentrability.

For compounds of this type made from tallow fatty acids having a Iodine Value of above 25, the ratio of cis to trans isomers has been found to be less critical unless very high concentrations are needed.

Other suitable examples of fabric softener actives are derived from fatty acyl groups wherein the terms "tallowyl" and "canolyl" in the above examples are replaced by the terms "cocoyl, palmyl, lauryl, oleyl, ricinoleyl, stearyl, palmityl," which correspond to the triglyceride source from which the fatty acyl units are derived. These alternative fatty acyl sources can comprise either fully saturated, or preferably at least partly unsaturated chains.

As described herein before, R units are preferably methyl, however, suitable fabric softener actives are described by replacing the term "methyl" in the above examples in Table II with the units "ethyl, ethoxy, propyl, propoxy, isopropyl, butyl, isobutyl and t-butyl".

The counter ion, X, in the examples of Table II can be suitably replaced by bromide, methylsulfate, formate, sulfate, nitrate, and mixtures thereof. In fact, the anion, X, is merely present as a counterion of the positively charged quaternary ammonium compounds. The nature of the counterion is not critical at all to the practice of the present invention. The scope of this invention is not considered limited to any particular anion.

The quaternary ammonium or their non-quaternized amine precursor compounds are present at levels of from about 1% to about 80% of compositions herein, depending on the composition execution which can be dilute with a preferred level of active from about 5% to about 15%, or concentrated, with a preferred level of active from about 15% to about 50%, most preferably about 15% to about 35%.

For the preceding fabric softening agents, the pH of the compositions herein is an important parameter of the present invention. Indeed, it influences the stability of the quaternary ammonium or amine precursors compounds, especially in prolonged storage conditions.

The pH, as defined in the present context, is measured in the neat compositions at 20° C. While these compositions are operable at pH of less than about 6.0, for optimum hydrolytic stability of these compositions, the neat pH, measured in the above-mentioned conditions, must be in the range of from about 2.0 to about 4.5, preferably about 2.0 to about 3.5. The pH of these compositions herein can be regulated by the addition of a Bronsted acid.

Examples of suitable acids include the inorganic mineral acids, carboxylic acids, in particular the low molecular weight ($C_1$–$C_5$) carboxylic acids, and alkylsulfonic acids. Suitable inorganic acids include HCl, $H_2SO_4$, $HNO_3$ and $H_3PO_4$. Suitable organic acids include formic, acetic, citric, methylsulfonic and ethylsulfonic acid. Preferred acids are citric, hydrochloric, phosphoric, formic, methylsulfonic acid, and benzoic acids.

As used herein, when the diester is specified, it will include the monoester that is normally present in manufacture. For softening, under no/low detergent carry-over laundry conditions the percentage of monoester should be as low as possible, preferably no more than about 2.5%. However, under high detergent carry-over conditions, some monoester is preferred. The overall ratios of diester to monoester are from about 100:1 to about 2:1, preferably from about 50:1 to about 5:1, more preferably from about 13:1 to about 8:1. Under high detergent carry-over conditions, the di/monoester ratio is preferably about 1:1. The level of monoester present can be controlled in the manufacturing of the softener compound.

Additional Softening Agents

Softening agents which are also useful in the compositions of the present invention are nonionic fabric softener materials, preferably in combination with cationic softening agents. Typically, such nonionic fabric softener materials have a HLB of from about 2 to about 9, more typically from about 3 to about 7. Such nonionic fabric softener materials tend to be readily dispersed either by themselves, or when combined with other materials such as single-long-chain alkyl cationic surfactant described in detail hereinafter. Dispersibility can be improved by using more single-long-chain alkyl cationic surfactant, mixture with other materials as set forth hereinafter, use of hotter water, and/or more agitation. In general, the materials selected should be relatively crystalline, higher melting, (e.g. >40° C.) and relatively water-insoluble.

The level of optional nonionic softener in the compositions herein is typically from about 0.1% to about 10%, preferably from about 1% to about 5%.

Preferred nonionic softeners are fatty acid partial esters of polyhydric alcohols, or anhydrides thereof, wherein the alcohol, or anhydride, contains from 2 to 18, preferably from 2 to 8, carbon atoms, and each fatty acid moiety contains from 12 to 30, preferably from 16 to 20, carbon atoms. Typically, such softeners contain from one to 3, preferably 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan. Sorbitan esters and polyglycerol monostearate are particularly preferred.

The fatty acid portion of the ester is normally derived from fatty acids having from 12 to 30, preferably from 16 to 20, carbon atoms, typical examples of said fatty acids being lauric acid, myristic acid, palmitic acid, stearic acid, oleic and behenic acid.

Highly preferred optional nonionic softening agents for use in the present invention are the sorbitan esters, which are esterified dehydration products of sorbitol, and the glycerol esters.

Commercial sorbitan monostearate is a suitable material. Mixtures of sorbitan stearate and sorbitan palmitate having stearate/palmitate weight ratios varying between about 10:1 and about 1:10, and 1,5-sorbitan esters are also useful.

Glycerol and polyglycerol esters, especially glycerol, diglycerol, triglycerol, and polyglycerol mono- and/or di-esters, preferably mono-, are preferred herein (e.g. polyglycerol monostearate with a trade name of Radiasurf 7248).

Useful glycerol and polyglycerol esters include monoesters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described hereinbefore for the sorbitan and glycerol esters.

Additional fabric softening agents useful herein are described in U.S. Pat. No. 4,661,269, issued Apr. 28, 1987, in the names of Toan Trinh, Errol H. Wahl, Donald M. Swartley, and Ronald L. Hemingway; U.S. Pat. No. 4,439,335, Burns, issued Mar. 27, 1984; and in U.S. Pat. Nos.: 3,861,870, Edwards and Diehl; 4,308,151, Cambre; 3,886,075, Bernardino; 4,233,164, Davis; 4,401,578, Verbruggen; 3,974,076, Wiersema and Rieke; 4,237,016, Rudkin, Clint, and Young; and European Patent Application publication No. 472,178, by Yamamura et al., all of said documents being incorporated herein by reference.

For the purposes of the present invention, the further suitable softening agents which are useful for inclusion in the rinse added fabric softening compositions of the present invention can be broadly classified into one of three general categories:

(a) the reaction product of higher fatty acids with a polyamine selected from the group consisting of hydroxyalkylalkylenediamines and dialkylenetriamines and mixtures thereof (preferably from about 10% to about 80%); and/or (b) cationic nitrogenous salts containing only one long chain acyclic aliphatic $C_{15}$–$C_{22}$ hydrocarbon group (preferably from about 3% to about 40%); and/or (c) cationic nitrogenous salts having two or more long chain acyclic aliphatic $C_{15}$–$C_{22}$ hydrocarbon groups or one said group and an arylalkyl group (preferably from about 10% to about 80%);

with said (a), (b) and (c) preferred percentages being by weight of the fabric softening agent component of the present invention compositions.

Following are the general descriptions of the preceding (a), (b), and (c) softener ingredients (including certain specific examples which illustrate, but do not limit the present invention).

Component (a)

Softening agents (actives) of the present invention may be the reaction products of higher fatty acids with a polyamine selected from the group consisting of hydroxyalkylalkylenediamines and dialkylenetriamines and mixtures thereof. These reaction products are mixtures of several compounds in view of the multi-functional structure of the polyamines.

The preferred Component (a) is a nitrogenous compound selected from the group consisting of the reaction product mixtures or some selected components of the mixtures. More specifically, the preferred Component (a) is a compound selected from the group consisting of substituted imidazoline compounds having the formula:

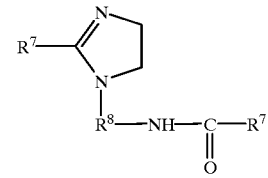

wherein $R^7$ is an acyclic aliphatic $C_{15}$–$C_{21}$ hydrocarbon group and $R^8$ is a divalent $C_1$–$C_3$ alkylene group.

Component (a) materials are commercially available as: Mazamide® 6, sold by Mazer Chemicals, or Ceranine® HC, sold by Sandoz Colors & Chemicals; stearic hydroxyethyl imidazoline sold under the trade names of Alkazine® ST by Alkaril Chemicals, Inc., or Schercozoline® S by Scher Chemicals, Inc.; N,N"-ditallowalkoyldiethylenetriamine; 1-tallowamidoethyl-2-tallowimidazoline (wherein in the preceding structure $R^1$ is an aliphatic $C_{15}$–$C_{17}$ hydrocarbon group and $R^8$ is a divalent ethylene group).

Certain of the Components (a) can also be first dispersed in a Bronsted acid dispersing aid having a pKa value of not greater than about 4; provided that the pH of the final composition is not greater than about 6. Some preferred dispersing aids are hydrochloric acid, phosphoric acid, or methylsulfonic acid.

Both N,N"-ditallowalkoyldiethylenetriamine and 1-tallow(amidoethyl)-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, Journal of the American Oil Chemicals' Society, January 1978, pages 118–121). N,N"-ditallow alkoyldiethylenetriamine and 1-tallowamidoethyl-2-tallowimidazoline can be obtained from Witco Chemical Company as experimental chemicals. Methyl-1-tallowamidoethyl-2-tallowimidazolinium methylsulfate is sold by Witco Chemical Company under the tradename Varisoft® 475.

Component (b)

The preferred Component (b) is a cationic nitrogenous salt containing one long chain acyclic aliphatic $C_{15}$–$C_{22}$ hydrocarbon group, preferably selected from acyclic quaternary ammonium salts having the formula:

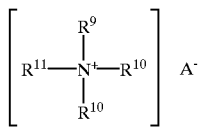

wherein $R^9$ is an acyclic aliphatic $C_{15}-C_{22}$ hydrocarbon group, $R^{10}$ and $R^{11}$ are $C_1-C_4$ saturated alkyl or hydroxy alkyl groups, and A– is an anion.

Examples of Component (b) are the monoalkyltrimethylammonium salts such as monotallowtrimethylammonium chloride, mono(hydrogenated tallow)trimethylammonium chloride, palmityltrimethyl ammonium chloride and soyatrimethylammonium chloride, sold by Witco Chemical Company under the trade name Adogen® 471, Adogen® 441, Adogen® 444, and Adogen® 415, respectively. In these salts, $R^9$ is an acyclic aliphatic $C_{16}-C_{18}$ hydrocarbon group, and $R^{10}$ and $R^{11}$ are methyl groups. Mono(hydrogenated tallow)trimethylammonium chloride and monotallowtrimethylammonium chloride are preferred.

Other examples of Component (b) are behenyltrimethylammonium chloride wherein $R^9$ is a $C_{22}$ hydrocarbon group and sold under the trade name Kemamine® Q2803-C by Humko Chemical Division of Witco Chemical Corporation; soyadimethylethylammonium ethylsulfate wherein $R^9$ is a $C_{16}-C_{18}$ hydrocarbon group, $R^{10}$ is a methyl group, $R^{11}$ is an ethyl group, and A– is an ethylsulfate anion, sold under the trade name Jordaquat® 1033 by Jordan Chemical Company; and methyl-bis(2-hydroxyethyl)-octadecylammonium chloride wherein $R^9$ is a $C_{18}$ hydrocarbon group, $R^{10}$ is a 2-hydroxyethyl group and $R^{11}$ is a methyl group and available under the trade name Ethoquad® 18/12 from Armak Company.

Other examples of Component (b) are 1-ethyl-1-(2-hydroxy ethyl)-2-isoheptadecylimidazolinium ethylsulfate, available from Mona Industries, Inc. under the trade name Monaquat® ISIES; mono(tallowoyloxyethyl) hydroxyethyldimethylammonium chloride, i.e., monoester of tallow fatty acid with di(hydroxyethyl)dimethylammonium chloride, a by-product in the process of making diester of tallow fatty acid with di(hydroxyethyl)dimethylammonium chloride, i.e., di(tallowoyloxyethyl) dimethylammonium chloride.

Component (c)

Preferred cationic nitrogenous salts having two or more long chain acyclic aliphatic $C_8-C_{22}$ hydrocarbon groups or one said group and an arylalkyl group which can be used either alone or as part of a mixture are selected from the group consisting of:

acyclic quaternary ammonium salts having the formula:

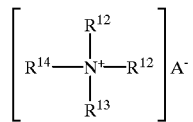

wherein $R^{12}$ is an acyclic aliphatic $C_8-C_{22}$ hydrocarbon group, $R^{13}$ is a $C_1-C_4$ saturated alkyl or hydroxyalkyl group, $R^{14}$ is selected from the group consisting of $R^{12}$ and $R^{13}$ groups, and A– is an anion defined as above.

Examples of Component (c) are the well-known dialkyldi methylammonium salts such as ditallowdimethylammonium chloride, ditallowdimethylammonium methylsulfate, di(hydrogenatedtallow)dimethylammonium chloride, distearyldimethylammonium chloride, dibehenyldimethylammonium chloride. Di(hydrogenatedtallow)di methylammonium chloride and ditallowdimethylammonium chloride are preferred. Examples of commercially available dialkyldimethyl ammonium salts usable in the present invention are di(hydrogenatedtallow)dimethylammonium chloride (trade name Adogen® 442), ditallowdimethylammonium chloride (trade name Adogen® 470), distearyl dimethylammonium chloride (trade name Arosurf® TA-100), all available from Witco Chemical Company. Dibehenyldimethylammonium chloride is sold under the trade name Kemamine Q-2802C by Humko Chemical Division of Witco Chemical Corporation.

Other examples of Component (c) are methylbis (tallowamidoethyl)(2-hydroxyethyl)ammonium methylsulfate and methylbis(hydrogenated tallowamidoethyl)(2-hydroxyethyl)ammonium methylsulfate; these materials are available from Witco Chemical Company under the trade names Varisoft® 222 and Varisoft® 110, respectively: dimethylstearylbenzyl ammonium chloride sold under the trade names Varisoft® SDC by Witco Chemical Company and Ammonyx® 490 by Onyx Chemical Company.

An even more preferred composition contains Component (a): the reaction product of about 2 moles of hydrogenated tallow fatty acids with about 1 mole of N-2-hydroxyethylethylenediamine and is present at a level of from about 20% to about 70% by weight of the fabric softening component of the present invention compositions; Component (b): mono(hydrogenated tallow)trimethyl ammonium chloride present at a level of from about 3% to about 30% by weight of the fabric softening component of the present invention compositions; Component (c): selected from the group consisting of di(hydrogenatedtallow) dimethylammonium chloride, ditallowdimethylammonium chloride, methyl-1-tallowamidoethyl-2-tallowimidazolinium methylsulfate, diethanol ester dimethylammonium chloride, and mixtures thereof; wherein Component (c) is present at a level of from about 20% to about 60% by weight of the fabric softening component of the present invention compositions; and wherein the weight ratio of said di(hydrogenated tallow)dimethylammonium chloride to said methyl-1-tallowamidoethyl-2-tallowimidazolinium methylsulfate is from about 2:1 to about 6:1.

In the cationic nitrogenous salts described hereinbefore, the anion A– provides charge neutrality. Most often, the anion used to provide charge neutrality in these salts is a halide, such as chloride or bromide. However, other anions can be used, such as methylsulfate, ethylsulfate, hydroxide, acetate, formate, citrate, sulfate, carbonate, and the like. Chloride and methylsulfate are preferred herein as anion A–.

Liquid Carrier

Another optional, but preferred, ingredient is a liquid carrier. The liquid carrier employed in the instant compositions is preferably at least primarily water due to its low cost, relative availability, safety, and environmental compatibility. The level of water in the liquid carrier is preferably at least about 50%, most preferably at least about 60%, by weight of the carrier. Mixtures of water and low molecular weight, e.g., <about 200, organic solvent, e.g., lower alcohols such as ethanol, propanol, isopropanol or butanol are useful as the carrier liquid. Low molecular weight alcohols include monohydric, dihydric (glycol, etc.) trihydric (glycerol, etc.), and higher polyhydric (polyols) alcohols.

Additional Solvents

The compositions of the present invention may comprise one or more solvents which provide increased ease of formulation. This is particularly the case when formulating liquid, clear fabric softening compositions. When employed, the ease of formulation solvent system preferably comprises less than about 40%, preferably from about 10% to about 35%, more preferably from about 12% to about 25%, and even more preferably from about 14% to about 20%, by weight of the composition. The ease of formulation solvent is selected to minimize solvent odor impact in the composition and to provide a low viscosity to the final composition. For example, isopropyl alcohol is not very effective and has a strong odor. n-Propyl alcohol is more effective, but also has a distinct odor. Several butyl alcohols also have odors but can be used for effective clarity/stability, especially when used as part of a ease of formulation solvent system to minimize their odor. The alcohols are also selected for optimum low temperature stability, that is they are able to form compositions that are liquid with acceptable low viscosities and translucent, preferably clear, down to about 40° F. (about 4.4° C.) and are able to recover after storage down to about 20° F. (about 6.7° C.).

The suitability of any ease of formulation solvent for the formulation of the liquid, concentrated, preferably clear, fabric softener compositions herein with the requisite stability is surprisingly selective. Suitable solvents can be selected based upon their octanol/water partition coefficient (P). Octanol/water partition coefficient of a ease of formulation solvent is the ratio between its equilibrium concentration in octanol and in water. The partition coefficients of the ease of formulation solvent ingredients of this invention are conveniently given in the form of their logarithm to the base 10, logP.

The logP of many ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each ingredient, and takes into account the numbers and types of atoms, the atom connectivity, and chemical bonding. These ClogP values, which are the most reliable and widely used estimates for this physicochemical property, are preferably used instead of the experimental logP values in the selection of the ease of formulation solvent ingredients which are useful in the present invention. Other methods that can be used to compute ClogP include, e.g., Crippen's fragmentation method as disclosed in J. Chem. Inf. Comput. Sci., 27, 21 (1987); Viswanadhan's fragmentation method as disclose in J. Chem. Inf. Comput. Sci., 29, 163 (1989); and Broto's method as disclosed in Eur. J. Med. Chem.—Chim. Theor., 19, 71 (1984).

The ease of formulation solvents herein are selected from those having a ClogP of from about 0.15 to about 0.64, preferably from about 0.25 to about 0.62, and more preferably from about 0.40 to about 0.60, said ease of formulation solvent preferably being at least somewhat asymmetric, and preferably having a melting, or solidification, point that allows it to be liquid at, or near room temperature. Solvents that have a low molecular weight and are biodegradable are also desirable for some purposes. The more assymetric solvents appear to be very desirable, whereas the highly symmetrical solvents such as 1 ,7-heptanediol, or 1,4-bis (hydroxymethyl) cyclohexane, which have a center of symmetry, appear to be unable to provide the essential clear compositions when used alone, even though their ClogP values fall in the preferred range.

The most preferred ease of formulation solvents can be identified by the appearance of the softener vesicles, as observed via cryogenic electron microscopy of the compositions that have been diluted to the concentration used in the rinse. These dilute compositions appear to have dispersions of fabric softener that exhibit a more unilamellar appearance than conventional fabric softener compositions. The closer to uni-lamellar the appearance, the better the compositions seem to perform. These compositions provide surprisingly good fabric softening as compared to similar compositions prepared in the conventional way with the same fabric softener active.

Operable ease of formulation solvents are disclosed and listed below which have ClogP values which fall within the requisite range. These include mono-ols, C6 diols, C7 diols, octanediol isomers, butanediol derivatives, trimethylpentanediol isomers, ethylmethylpentanediol isomers, propyl pentanediol isomers, dimethylhexanediol isomers, ethylhexanediol isomers, methylheptanediol isomers, octanediol isomers, nonanediol isomers, alkyl glyceryl ethers, di(hydroxy alkyl) ethers, and aryl glyceryl ethers, aromatic glyceryl ethers, alicyclic diols and derivatives, $C_3C_7$ diol alkoxylated derivatives, aromatic diols, and unsaturated diols. Particularly preferred ease of formulation solvents include hexanediols such as 1,2-Hexanediol and 2-Ethyl-1, 3-hexanediol and pentanediols such as 2,2,4-Trimethyl-1,3-pentanediol. These ease of formulation solvents are all disclosed in copending U.S. patent application Ser. Nos. 08/621,019; 08/620,627; 08/620,767; 08/620,513; 08/621, 285; 08/621,299; 08/621,298; 08/620,626; 08/620,625; 08/620,772; 08/621,281; 08/620,514; and 08/620,958, all filed Mar. 22, 1996 and all having the title "CONCENTRATED, STABLE, PREFERABLY CLEAR, FABRIC SOFTENING COMPOSITION", the disclosures of which are all herein incorporated by reference.

Concentration Aids

Concentrated compositions of the present invention may require organic and/or inorganic concentration aids to go to even higher concentrations and/or to meet higher stability standards depending on the other ingredients. Surfactant concentration aids are typically selected from the group consisting of single long chain alkyl cationic surfactants; nonionic surfactants; amine oxides; fatty acids; or mixtures thereof, typically used at a level of from 0 to about 15% of the composition.

Inorganic viscosity/dispersibility control agents which can also act like or augment the effect of the surfactant concentration aids, include water-soluble, ionizable salts which can also optionally be incorporated into the compositions of the present invention. A wide variety of ionizable salts can be used. Examples of suitable salts are the halides of the Group IA and IIA metals of the Periodic Table of the Elements, e.g., calcium chloride, magnesium chloride, sodium chloride, potassium bromide, and lithium chloride. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 20,000 parts per million (ppm), preferably from about 20 to about 11,000 ppm, by weight of the composition.

Alkylene polyammonium salts can be incorporated into the composition to give viscosity control in addition to or in place of the water-soluble, ionizable salts above. In addition, these agents can act as scavengers, forming ion pairs with anionic detergent carried over from the main wash, in the rinse, and on the fabrics, and may improve softness performance. These agents may stabilize the viscosity over a broader range of temperature, especially at low temperatures, compared to the inorganic electrolytes.

Specific examples of alkylene polyammonium salts include 1-lysine monohydrochloride and 1,5-diammonium 2-methyl pentane dihydrochloride.

Other Ingredients

Still other optional ingredients include, but are not limited to Soil Release Agents, perfumes, preservatives/stabilizers, chelants, bacteriocides, colorants, optical brighteners, antifoam agents, and the like.

Soil Release Agents

Soil Release agents are desirably used in fabric softening compositions of the instant invention. Suitable soil release agents include those of U.S. Pat. No. 4,968,451, November 6, 1990 to J. J. Scheibel and E. P. Gosselink: such ester oligomers can be prepared by (a) ethoxylating allyl alcohol, (b) reacting the product of (a) with dimethyl terephthalate ("DMT") and 1,2-propylene glycol ("PG") in a two-stage transesterification/oligomerization procedure and (c) reacting the product of (b) with sodium metabisulfite in water; the nonionic end-capped 1,2-propylene/polyoxyethylene terephthalate polyesters of U.S. Pat. No. 4,711,730, Dec. 8, 1987 to Gosselink et al, for example those produced by transesterification/oligomerization of poly(ethyleneglycol) methyl ether, DMT, PG and poly(ethyleneglycol) ("PEG"); the partly- and fully-anionic-end-capped oligomeric esters of U.S. Pat. No. 4,721,580, Jan. 26, 1988 to Gosselink, such as oligomers from ethylene glycol ("EG"), PG, DMT and Na-3,6-dioxa-8-hydroxyoctanesulfonate; the nonionic-capped block polyester oligomeric compounds of U.S. Pat. No. 4,702,857, Oct. 27, 1987 to Gosselink, for example produced from DMT, Me-capped PEG and EG and/or PG, or a combination of DMT, EG and/or PG, Me-capped PEG and Na-dimethyl-5-sulfoisophthalate; and the anionic, especially sulfoaroyl, end-capped terephthalate esters of U.S. Pat. No. 4,877,896, Oct. 31, 1989 to Maldonado, Gosselink et al, the latter being typical of SRA's useful in both laundry and fabric conditioning products, an example being an ester composition made from m-sulfobenzoic acid monosodium salt, PG and DMT optionally but preferably further comprising added PEG, e.g., PEG 3400. Another preferred soil release agent is a sulfonated end-capped type described in U.S. Pat. No. 5,415,807.

Perfumes

While the pro-fragrances of the present invention can be used alone and simply mixed with essential fabric softening ingredient, most notably surfactant, they can also be desirably combined into three-part formulations which combine (a) a non-fragranced fabric softening base comprising one or more synthetic fabric softeners, (b) one or more pro-fragrant β-keto-esters in accordance with the invention and (c) a fully-formulated fragrance. The latter provides desirable in-package and in-use (wash-time) fragrance, while the pro-fragrance provides a long-term fragrance to the laundered textile fabrics.

In formulating the present fabric softening compositions, the fully-formulated fragrance can be prepared using numerous known odorant ingredients of natural or synthetic origin. The range of the natural raw substances can embrace not only readily-volatile, but also moderately-volatile and slightly-volatile components and that of the synthetics can include representatives from practically all classes of fragrant substances, as will be evident from the following illustrative compilation: natural products, such as tree moss absolute, basil oil, citrus fruit oils (such as bergamot oil, mandarin oil, etc.), mastix absolute, myrtle oil, palmarosa oil, patchouli oil, petitgrain oil Paraguay, wormwood oil, alcohols, such as farnesol, geraniol, linalool, nerol, phenylethyl alcohol, rhodinol, cinnamic alcohol, aldehydes, such as citral, Helional™, alpha-hexyl-cinnamaldehyde, hydroxycitronellal, Lilial™ (p-tert-butyl-alpha-methyldihydrocinnamaldehyde), methylnonylacetaldehyde, ketones, such as allylionone, alpha-ionone, beta-ionone, isoraldein (isomethyl-alpha-ionone), methylionone, esters, such as allyl phenoxyacetate, benzyl salicylate, cinnamyl propionate, citronellyl acetate, citronellyl ethoxolate, decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, etc., lactones, such as gamma-undecalactone, various components often used in perfumery, such as musk ketone, indole, p-menthane-8-thiol-3-one, and methyl-eugenol. Likewise, any conventional fragrant acetal or ketal known in the art can be added to the present composition as an optional component of the conventionally formulated perfume (c). Such conventional fragrant acetals and ketals include the well-known methyl and ethyl acetals and ketals, as well as acetals or ketals based on benzaldehyde, those comprising phenylethyl moieties, or more recently developed specialties such as those described in a United States patent entitled "Acetals and Ketals of Oxo-Tetralins and Oxo-Indanes", see U.S. Pat. No. 5,084,440, issued Jan. 28, 1992, assigned to Givaudan Corp. Of course, other recent synthetic specialties can be included in the perfume compositions for fully-formulated fabric softening compositions. These include the enol ethers of alkyl-substituted oxo-tetralins and oxo-indanes as described in U.S. Pat. No. 5,332,725, Jul. 26, 1994, assigned to Givaudan; or Schiff Bases as described in U.S. Pat. No. 5,264,615, Dec. 9, 1991, assigned to Givaudan. It is preferred that the pro-fragrant material be added separately from the conventional fragrances to the fabric softening compositions of the invention.

Stabilizers

Stabilizers can be present in the compositions of the present invention. The term "stabilizer," as used herein, includes antioxidants and reductive agents. These agents are present at a level of from 0% to about 2%, preferably from about 0.01% to about 0.2%, more preferably from about 0.035% to about 0.1% for antioxidants, and more preferably from about 0.01% to about 0.2% for reductive agents. These assure good odor stability under long term storage conditions for the compositions and compounds stored in molten form. The use of antioxidants and reductive agent stabilizers is especially critical for low scent products (low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox S-1; a mixture of BHT (butylated hydroxytoluene), BHA (butylated hydroxyanisole), propyl gallate, and citric acid, available from Eastman Chemical Products, Inc., under the trade name Tenox-6; butylated hydroxytoluene, available from UOP Process Division under the trade name Sustane® BHT; tertiary butylhydroquinone, Eastman Chemical Products, Inc., as Tenox TBHQ; natural tocopherols, Eastman Chemical Products, Inc., as Tenox GT-1/GT-2; and butylated hydroxyanisole, Eastman Chemical Products, Inc., as BHA; long chain esters ($C_8$–$C_{22}$) of gallic acid, e.g., dodecyl gallate; Irganox® 1010; Irganox® 1035; Irganox® B 1171; Irganox® 1425; Irganox® 3114; Irganox® 3125; and mixtures thereof; preferably Irganox® 3125, Irganox® 1425, Irganox® 3114, and mixtures thereof; more preferably Irganox® 3125 alone or mixed with citric acid and/or other chelators such as isopropyl citrate, Dequest® 2010, available from Monsanto with a chemical name of 1-hydroxyethylidene-1,1-diphosphonic acid (etidronic acid), and Tiron®, available from Kodak with a chemical name of 4,5-dihydroxy-m-benzene-sulfonic acid/sodium salt, EDDS, and DTPA®, available from Aldrich with a chemical name of diethylenetriaminepentaacetic acid. The chemical names and CAS numbers for some of the above stabilizers are listed in Table II below.

TABLE II

| Antioxidant | CAS No. | Chemical Name used in Code of Federal Regulations |
|---|---|---|
| Irganox ® 1010 | 6683-19-8 | Tetrakis (methylene(3,5-di-tert-butyl-4hydroxyhydrocinnamate))methane |
| Irganox ® 1035 | 41484-35-9 | Thiodiethylene bis(3,5-di-tert-butyl-4-hydroxyhydrocinnamate |
| Irganox ® 1098 | 23128-74-7 | N,N'-Hexamethylene bis(3,5-di-tert-butyl-4-hydroxyhydro-cinnamamide |
| Irganox ® B 1171 | 31570-04-4 23128-74-7 | 1:1 Blend of Irganox ® 1098 and Irgafos ® 168 |
| Irganox ® 1425 | 65140-91-2 | Calcium bis(monoethyl(3,5-di-tert-butyl-4-hydroxybenzyl)-phosphonate) |
| Irganox ® 3114 | 65140-91-2 | Calcium bis(monoethyl(3,5-di-tert-butyl-4-hydroxybenzyl)-phosphonate) |
| Irganox ® 3125 | 34137-09-2 | 3,5-Di-tert-butyl-4-hydroxy-hydrocinnamic acid triester with 1,3,5-tris(2-hydroxyethyl)-S-triazine-2,4,6-(1H, 3H, 5H)-trione |
| Irgafos ® 168 | 31570-04-4 | Tris(2,4-di-tert-butyl-phenyl)-phosphite |

Examples of reductive agents include sodium borohydride, hypophosphorous acid, Irgafos® 168, and mixtures thereof.

The following examples illustrate the β-keto-esters and compositions of this invention, but are not intended to be limiting thereof.

EXAMPLE 1

Preparation of 3,7-Dimethyl-1,6-octadien-3-yl 3-(β-naphthyl-3-oxo-propionate

Lithium diisopropylamide (101.0 mL of a 2.0M solution, 0.202 mol) is placed into a 500 mL three-necked round-bottomed flask fitted with a magnetic stirrer, internal thermometer, argon inlet, and addition funnel. The flask is placed in a dry ice-acetone bath. 3,7-Dimethyl-1,6-octadien-3-yl acetate (linalyl acetate) in the amount of (18.66 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.43 g, 0.090 mol) dissolved in THF (25 mL) over 30 min. The mixture is warmed to –20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and GC analysis and the structure confirmed by mass spectrometry, $^1H$ and $^{13}C$ NMR.

EXAMPLE 2

Preparation of 2,6-Dimethyl-7-octen-2-yl 3-(4-Methoxyphenyl)-3-oxo-propionate

N-Isopropylcyclohexylamine (25.00 g, 0.177 mol) and THF in the amount of 200 mL is placed into a 1000 mL three-necked round-bottomed flask fitted with a magnetic stirrer, internal thermometer, argon inlet, and addition funnel. The flask is placed in a ice-methanol bath cooled to –5° C. and its contents treated with n-butyllithium in the amount of (70.8 mL of a 2.50 M solution, 0.177 mol). The mixture is stirred for 20 min and then cooled to –78° C. 2,6-Dimethyl-7-octen-2-yl acetate (dihydromyrcenyl acetate) in the amount of (17.55 g, 0.089 mol) is dissolved in THF (10 mL) and the resulting solution added to the flask over 45 min. Once addition is complete, the mixture is stirred for an additional 15 min before being treated with a solution of p-methoxybenzoyl chloride in the amount of (15.10 g, 0.090 mol) dissolved in THF (25 ml) over 30 min and then stirred for 1 h. The mixture is warmed to 0° C. and then treated with 90 mL of 20% HCl an hour later. The mixture is poured into a separatory funnel containing ether (100 ml) and water (200 ml). The aqueous layer is extracted with ether (100 ml). The combined organic layers are washed with saturated $NaHCO_3$ solution (2×100 ml), water (2×100 ml) and brine (100 ml), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and the structure confirmed by $^1H$ and $^{13}C$ NMR.

EXAMPLE 3

Preparation of 2,6-Dimethyl-7-octen-2-yl 3-(4-nitrophenyl)-3-oxo-propionate

Lithium diisopropylamide (121.0 mL of a 2.0M solution, 0.243 mol) is placed into a 500 mL three-necked round-bottomed flask fitted with a magnetic stirrer, internal thermometer, argon inlet, and addition funnel. The flask is placed in a dry ice-acetone bath. 2,6-Dimethyl-7-octen-2-yl acetate (22.66 g, 0.114 mol) is dissolved in THF (5 mL) and the resulting solution added to the flask over 45 min. Once addition is complete, the mixture is stirred for an additional 15 min. before being treated with a solution of 4-nitrobenzoyl chloride (20.00 g, 0.108 mol) dissolved in THF (25 mL) over 30 min. The mixture is warned to –20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated $NaHCO_3$ solution (2× 100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 4

Preparation of 2,6-Dimethyl-7-octen-2-yl 3-(β-naphthyl)-3-oxo-propionate

Lithium diisopropylamide in the amount of (100.0 mL of a 2.0 M solution, 0.201 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate in the amount of (18.75 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.00 g, 0.089 mol) dissolved in THF (25 mL) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate dissolved in petroleum ether) to give an oil. Purity of the product is determined by thin layer chromatography and the structure confirmed by $^1$H and $^{13}$C NMR.

EXAMPLE 5

Preparation of 3,7-Dimethyl-1,6-octadien-3-yl 3-(4-Methoxyphenyl)-3-oxo-propionate Lithium diisopropylamide (119.0 mL of a 2.0M solution, 0.238 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (22.04 g, 0.112 mol) is dissolved in THF (5 mL) and the resulting solution added to the flask over 45 min. Once addition is complete, the mixture is stirred for an additional 15 min. before being treated with a solution of p-anisoyl chloride (35.00 g, 0.106 mol) dissolved in THF (30 mL) over 30 min. The mixture is warmed to −20° C. and stirred at that temperature for 18 h. After warming to 0° C., the mixture is quenched with 20% HCl (80 mL). The mixture is poured into a separatory funnel containing ether (150 mL) and water (250 mL). The aqueous layer is extracted with ether (150 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an oil. The oil is purified by column chromatography (elution with 2% ethyl acetate/petroleum ether) to yield a colorless oil having $^1$H and $^{13}$C NMR spectra consistent with the desired product.

EXAMPLE 6

Preparation of (α,α-4-Trimethyl-3-cyclohexenyl)methyl 3-(β-naphthyl)-3-oxo-propionate Lithium diisopropylamide (171.0 mL of a 2.0M solution, 0.342 mol) is placed into a 1000 mL three-necked round-bottomed flask fitted with a magnetic stirrer, internal thermometer, argon inlet, and addition funnel. The flask is cooled to −78° C. (α,α-4-Trimethyl-3-cyclohexenyl)methyl acetate (30.00 g, 0.153 mol) is dissolved in THF (10 mL) and the resulting solution added to the flask over 45 min. Once addition is complete, the mixture is stirred for an additional 15 min. before being treated with a solution of 2-naphthoyl chloride (29.00 g, 0.152 mol) dissolved in THF (50 mL) over 30 min. The mixture is warmed to −20° C. and stirred at that temperature for 18 h. After warming to 0° C., the mixture is quenched with 20% HCl (105 mL). The mixture is poured into a separatory funnel containing ether (150 mL) and water (250 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an oil. The oil is purified by column chromatography (elution with 2% ethyl acetate/petroleum ether) to yield a semi-white solid which is triturated in cold n-pentane to yield a white powder having $^1$H and $^{13}$C NMR spectra consistent with the desired product.

EXAMPLE 7

Preparation of 3,7-Dimethyl-1,6-octadien-3-yl 3-(α-Naphthyl)-3-oxo-propionate Lithium diisopropylamide (96.3 mL of a 2.0M solution, 0.193 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (17.81 g, 0.091 mol) is dissolved in THF (5 mL) and the resulting solution added to the flask over 45 min. Once addition is complete, the mixture is stirred for an additional 15 min. before being treated with a solution of 1-naphthoyl chloride (16.82 g, 0.086 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an oil. The oil is purified by column chromatography (elution with 2% ethyl acetate/petroleum ether) to yield a colorless oil having $^1$H and $^{13}$C NMR spectra consistent with the desired product.

EXAMPLE 8

Preparation of cis 3-Hexen-1-yl 3-(β-Naphthyl)-3-oxo-propionate

Lithium diisopropylamide (133.0 mL of a 2.0M solution, 0.266 mol) is placed into a 500 mL three-necked round-bottomed flask fitted with a magnetic stirrer, internal thermometer, argon inlet, and addition funnel. The flask is cooled to −78° C. cis 3-Hexenyl acetate (17.80 g, 0.125 mol) is dissolved in THF (10 mL) and the resulting solution added to the flask over 45 min. Once addition is complete, the mixture is stirred for an additional 15 min. before being treated with a solution of 2-naphthoyl chloride (22.51 g, 0.118 mol) dissolved in THF (30 mL) over 30 min. The mixture is warmed to −20° C. and stirred at that temperature

EXAMPLE 9

Preparation of 9-Decen-1-yl 3-(β-Naphthyl)-3-oxo-propionate for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 9

Preparation of 9-Decen-1-yl 3-(β-Naphthyl)-3-oxo-propionate

Lithium diisopropylamide (79.8 mL of a 2.0M solution, 0.160 mol) is placed into a 250 mL three-necked round-bottomed flask fitted with a magnetic stirrer, internal thermometer, argon inlet, and addition funnel. The flask is cooled to −78° C. 9-Decen-1-yl acetate (14.91 g, 0.075 mol) is dissolved in THF (5 mL) and the resulting solution added to the flask over 45 min. Once addition is complete, the mixture is stirred for an additional 15 min. before being treated with a solution of 2-naphthoyl chloride (13.80 g, 0.071 mol) dissolved in THF (25 mL) over 30 min. The mixture is warmed to −20° C. and stirred at that temperature for 18 h. After warming to 0° C., the mixture is quenched with 20% HCl (47 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 10

Preparation of 3,7-Dimethyl-1,6-octadien-3-yl 3-(Nonanyl)-3-oxo-propionate

Lithium diisopropylamide (133.7 mL of a 2.0M solution, 0.267 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (24.73 g, 0.126 mol) is dissolved in THF (40 mL) and the resulting solution added to the flask over 45 min. Once addition is complete, the mixture is stirred for an additional 15 min. before being treated with a solution of nonanoyl chloride (21.88 g, 0.119 mol) over 30 min. The mixture is warmed to −20° C. and stirred at that temperature for 18 h. After warming to 0° C., the mixture is quenched with 20% HCl (60 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 11

Preparation of 2,6-Dimethyl-7-octen-2-yl 3-(Nonanyl)-3-oxo-propionate

Lithium diisopropylamide (75.7 mL of a 2.0M solution, 0.151 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate (14.14 g, 0.071 mol) is dissolved in THF (20 mL) and the resulting solution added to the flask over 45 min. Once addition is complete, the mixture is stirred for an additional 15 min. before being treated with a solution of nonanoyl chloride (12.38 g, 0.067 mol) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 12

Preparation of 3,7-Dimethyl-1,6-octadien-3-yl 3-Oxo-butyrate

A mixture of linalool (100 g, 0.648 mol) and 4-dimethylaminopyridine (0.40 g, 3.20 mmol) in a 500 mL three-necked round-bottomed flask fitted with a condenser, argon inlet, addition funnel, magnetic stirrer and internal thermometer is heated to 55° C. Diketene (54.50 g, 0.648 mol) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromtography (elution with dichloromethane) yields the desired product in 92% yield and nearly colorless.

EXAMPLE 13

Preparation of 2,6-Dimethyl-7-octen-2-yl 3-Oxo-butyrate

A mixture of dihydromyrcenol (37.88 g, 0.240 mol) and 4-dimethylaminopyridine (0.16 g, 1.30 mmol) in a 100 mL three-necked round-bottomed flask fitted with a condenser, argon inlet, addition funnel, magnetic stirrer and internal thermometer is heated to 50–60° C. Diketene (20.16 g, 0.240 mol) is added dropwise in the course of 15 min. The mixture has a slight exotherm and turned from yellow to red during this time. After stirring an additional hour at 50 C, the mixture is cooled to room temperature. At this point, NMR analysis indicates the reaction is complete. Purification of the product mixture by flash chromatography (elution with dichloromethane) yields the desired product in 95% yield as a nearly colorless oil.

EXAMPLE 14

Preparation of 3,7-Dimethyl-1,6-octadien-3-yl 3-(β-Naphthyl)-3-oxo-propionate

Crude 3,7-dimethyl-1,6-octadien-3-yl 3-oxo-butyrate (154.51, 0.648 mol) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to ~1 with 20% HCl. The mixture is transferred to a separatory funnel containing diethyl ether (500 mL) and water (500 mL). The layers are separated and the organic phase is washed with saturated $NaHCO_3$ solution (2×500 mL), dried over $MgSO_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoyl)acetate. A portion of this material is purified by column chromatography (elution with 2.5% ethyl acetate in hexanes) to give the desired product as a light yellow oil.

EXAMPLE 15

Preparation of 3,7-Dimethyl-1,6-octadien-3-yl 3-(β-Naphthyl)-3-oxo-2,2-dimethylpropionate Sodium hydride (2.30 g, 0.057 mol, 60%) and tetrahydrofuran (50 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (8.94 g, 0.025 mol) dissolved in 50 mL of tetrahydrofuran is added dropwise to the flask over 30 min. During addition, the mixture evolves gas. After stirring for 1 h, methyl iodide (7.24 g, 0.051 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 16

Preparation of 3,7-Dimethyl-1,6-octadien-3-yl 3-(β-naphthyl-3-oxo-2-methylpropionate Sodium hydride (3.92 g, 0.098 mol, 60%) and tetrahydrofuran (100 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (15.28 g, 0.044 mol) dissolved in 50 mL of tetrahydrofuran is added dropwise to the flask over 30 min. During addition, the mixture evolves gas. After stirring for 1 h, methyl iodide (10.65 g, 0.075 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 17

Preparation of 3,7-Dimethyl-1,6-octadien-3-yl 3-(Hexyl)-3-oxo-propionate 3,7-Dimethyl-1,6-octadien-3-yl 3-oxo-butyrate (30.00 g, 0.126 mol), dichloromethane (50 mL) and methyl ethyl ketone (10 mL) are combined in a 500 mL three-necked round-bottomed flask fitted with an internal thermometer, addition funnel, condenser and argon inlet. Calcium hydroxide (9.80 g, 0.132 mol, powdered) is added to the flask and the slurry stirs for 1 h. Heptanoyl chloride (17.84 g, 0.120 mol) in 10 ml of dichloromethane is added over 15 min so as to keep the reaction temperature between 35–40° C. The reaction continues to stir at 35–40° C. for 2 h. Ammonium chloride (7.06 g, 0.132 mol) dissolved in 20 mL of water is added to the flask. After 20 min, concentrated ammonium hydroxide is added to the mixture to adjust the pH to ~9.0. After 1 h, 20% HCl solution is added to drop the pH to ~1.0. After 1 h, the mixture is poured into 300 mL of dichloromethane. The layers are separated and the aqueous phase extracted with 100 mL of dichloromethane. The combine organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 18

Preparation of 3,7-Dimethyl-1,6-octadien-3-yl 3-Oxo-2-benzylbutyrate

Potassium carbonate (3.92 g, 0.028 mol), 3,7-dimethyl-1,6-octadien-3-yl 3-oxo-butyrate (4.80 g, 0.030 mol), benzyl chloride (4.80 g, 0.038 mol) and acetone (15 mL) are placed in a 50 mL round-bottomed flask fitted with a magnetic stirrer, condenser and argon inlet. The mixture is heated to reflux for 18 h. The cooled mixture is filtered and concentrated by rotary evaporation. The resulting oil is purified on silica gel to yield the desired compound. Structure is confirmed by thin layer chromatography and $^1H$ and $^{13}C$ NMR.

Examples of Liquid Fabric Softener Compositions Containing β-Keto-Ester Pro-perfumes

| Formulation Example: Ingredient | A Wt. % | B Wt. % | C Wt. % | D Wt. % | E Wt. % | F Wt. % |
|---|---|---|---|---|---|---|
| DEQA[1] | 25.0 | 23.3 | 23.3 | 23.3 | 25.0 | 23.3 |
| Ethanol | 4.0 | 3.65 | 3.65 | 3.65 | 4.0 | 3.65 |
| HCl | 0.01 | 0.74 | 0.74 | 0.74 | 0.01 | 0.74 |
| Chelant[2] | — | 2.50 | 2.50 | 2.50 | — | 2.50 |
| Ammonium Chloride | — | 0.10 | 0.10 | 0.10 | — | 0.10 |
| $CaCl_2$ | 0.46 | 0.50 | 0.50 | 0.50 | 0.46 | 0.50 |

-continued

| Formulation Example: Ingredient | A Wt. % | B Wt. % | C Wt. % | D Wt. % | E Wt. % | F Wt. % |
|---|---|---|---|---|---|---|
| Silicone Antifoam[3] | 0.15 | 0.15 | 0.15 | 0.15 | 0.15 | 0.15 |
| Preservative[4] | 0.0003 | 0.0003 | 0.0003 | 0.0003 | 0.0003 | 0.0003 |
| Perfume | — | — | 1.35 | 1.35 | 1.20 | 1.00 |
| Soil Release Polymer[5] | 0.50 | 0.75 | 0.75 | 0.75 | 0.50 | 0.75 |
| Product of Example 3[6] | 0.50 | 0.25 | — | 0.25 | — | — |
| Product of Example 11[7] | — | — | 0.60 | — | — | — |
| Product of Example 12[8] | — | — | — | — | 1.0 | — |
| Product of Example 14[9] | — | — | — | — | — | 1.0 |
| Water | 69.38 | 68.06 | 66.36 | 66.71 | 67.68 | 66.31 |

[1]·Di-(soft-tallowyloxyethyl) dimethyl ammonium chloride
[2]·Diethylenetriamine Pentaacetic acid(3) DC-2310, sold by Dow-Corning
[3]·DC-2310, sold by Dow-Corning
[4]·Kathon CG, sold by Rohm & Has
[5]·Copolymer of propylene terephthalate and ethyleneoxide
[6]·2,6-dimethyl-7-octen-2-yl 3-(4-nitrophenyl)-3-oxo-propionate.
[7]·2,6-dimethyl-7-octen-2-yl 3-(nonanyl)-3-oxo-propionate.
[8]·3,7-dimethyl-1,6-octadien-3-yl 3-oxo-butyrate.
[9]·3,7-dimethyl-1,6-octadien-3-yl (3-(β-naphthyl)-3-oxo-propionate.

Process

Example A is made in the following manner: A blend of 250g DEQA[1] and 40 g ethanol are melted at about 70° C. A 25% aqueous solution of HCl in the amount of 40 g is added to about 700 g of deionized water also at 70° C. containing the antifoam. The DEQA/alcohol blend is added to the water/HCl over a period of about five minutes with very vigorous agitation (IKA Paddle Mixer, model RW 20 DZM at 1500 rpm). A 25% aqueous solution of $CaCl_2$ in the amount of 13.8 g is added to the dispersion dropwise over 1 minute, followed by milling with an IKA Ultra Turrax T-50 high shear mill for 5 minutes. The dispersion is then cooled to room temperature by passing it through a plate and frame heat exchanger. Following cool-down, the soil release polymer is added into the dispersion in the form of a 40% solution and stirred for 10 minutes. The product of Example 1 in the amount of 5.0 g is blended into the dispersion with moderate agitation. Finally, another 4.6 g of 25% $CaCl_2$ is mixed into the dispersion and stirred for several hours.

Examples E is made in a like manner, excepting that the pro-perfume material is blended with the perfume component and the resulting mixture is added to the cooled product.

Example B is made in the following manner: A blend of 233 g DEQA[1] and 36.5 g ethanol are melted at about 75° C. A 25% aqueous solution of HCl in the amount of 0.3 g is added to about 680 g of deionized water also at 75° C. containing the antifoam. The DEQA/alcohol blend is added to the water/HCl over a period of about two minutes with very vigorous agitation (IKA Padel Mixer, model RW 20 DZM at 1500 rpm). A 2.5% aqueous solution of $CaCl_2$ in the amount of 2.5 g is added to the dispersion dropwise over 5 minutes, Meanwhile, 61 g of a 41% aqueous solution of the chelant is acidified by the addition of a 25% solution of HCl to a measured pH of 3. A small amount, about 8g, of the acidified chelant solution is stirred into the dispersion, followed by milling with an IKA Ultra Turrax T-50 high shear mill for 5 minutes. The dispersion is then cooled to room temperature.

Following cool-down, the soil release polymer is added into the dispersion in the form of a 40% solution and stirred for 10 minutes. The remaining acidified chelant solution is added over 3 minutes. The product of Example 1 in the amount of 2.5g is added, followed by the addition of ammonium chloride in the form of a 20% aqueous solution. Finally, the remaining $CaCl_2$ is added in the form of a 25% solution.

Examples C, D and F are made in a like manner, excepting that the pro-perfume material is blended with the perfume component and the resulting mixture is added to the cooled product.

Additional Formulation Examples

| Ingredient | G Wt. % | H Wt. % | I Wt. % | J Wt. % |
|---|---|---|---|---|
| DEQA[1] | 19.2 | 19.2 | 18.2 | 19.2 |
| Isopropyl alcohol | 3.1 | 3.1 | 2.9 | 3.1 |
| Tallow Alcohol Ethoxylate-25 | — | — | 1.20 | — |
| Poly(glycerol monostearate) | — | — | 2.40 | — |
| HCl | 0.02 | 0.02 | 0.08 | 0.02 |
| $CaCl_2$ | 0.12 | 0.12 | 0.18 | 0.12 |
| Silicone Antifoam | 0.02 | 0.02 | 0.02 | 0.02 |
| Soil Release Polymer[2] | 0.19 | 0.19 | 0.19 | 0.19 |
| Poly(ethyleneglycol) 4000MW | 0.60 | 0.60 | 0.60 | 0.60 |
| Perfume | 0.70 | 0.70 | 0.70 | 0.40 |
| Product of Example 3[3] | 0.58 | — | — | — |
| Product of Example 12[4] | — | 1.0 | 0.50 | — |
| Product of Example 13[5] | — | — | 0.50 | — |
| Product of Example 7[6] | — | — | — | 1.0 |
| Water | 75.47 | 75.05 | 72.53 | 75.35 |

[1]·Di-(hardtallowyloxyethyl) dimethyl ammonium chloride
[2]·Copolymer of propylene terephthalate and ethyleneoxide
[3]·3,7-dimethyl-1,6-octadien-3-yl 3-(β-naphthyl)-3-oxo-propionate.
[4]·3,7-dimethyl-1,6-octadien-3-yl 3-(nonanyl)-3-oxo-propionate.
[5]·2,6-dimethyl-7-octen-2-yl 3-(nonanyl)-3-oxo-propionate.
[6]·3,7-dimethyl-1,6-octadien-3-yl 3-(4-methoxyphenyl)-3-oxo-propionate Additional Examples of Liquid Fabric Softener Compositions Containing Pro-perfumes

| Formulation Example: Ingredient | K Wt. % | L Wt. % | M Wt. % |
|---|---|---|---|
| DEQA[1] | 10.35 | 10.35 | 10.35 |
| Ethanol | 1.40 | 1.40 | 1.40 |
| HCl | 0.0219 | 0.0219 | 0.0219 |
| Blue Dye | 0.0045 | 0.0045 | 0.0045 |
| Silicone Antifoam[2] | 0.015 | 0.015 | 0.015 |
| Low Salt Kathon[3] | 0.02 | 0.02 | 0.02 |
| $CaCl_2$ | * | * | * |
| Product of Example 1[4] | 0.25 | 0.50 | — |
| Water | 87.76 | 87.76 | 87.43 |

*Added as needed to adjust viscosity
[1]·Di-(hardtallowyloxyethyl) dimethyl ammonium chloride
[2]·Silicone DC-2310, sold by Dow-Corning
[3]·Kathon CG, sold by Rohm & Haas
[4]·3,7-dimethyl-1,6-octadien-3-yl 3-(β-naphthyl)-3-oxo-proprionate.

N. Experimental Procedure

A batch process is used. The procedure is divided in two parts: the preparation of the base product (prepared in the lab. without perfume and technology) and the addition of the perfume and the technology(ies).

Base product (to prepare a batch of 17 kg of base)
  i. The main tank is loaded with the water needed (15.1 kg) and is heated to 43° C. Start agitation at 800 rpm and mix blue dye. The mixer used is a Lightnin model LIU08.
  ii. Add HCl (3.8 g) by hand (31% activity).
  iii. Preheat DEQA (I)/ethanol at 75° C. (1760 g at 85% actives level) and inject into tank with water at a rate of 22 ml/min.

iv. Manually add low salt Kathon (3.4 g) and silicone antifoam (25.7 g).

v. Mix about 5 minutes

Finished product preparation (to prepare 0.250 kg of finished product composition)

vi. The product of Example 1 (0.625 g) is added to a 249 g aliquot of the above product by mixing with an IKA Ultra Turrax T-50 at 6000 rpm for 15 minutes.

Examples L and M are made in a like manner, except that the pro-perfume material is added at the required amount.

What is claimed is:

1. A rinse added fabric softening composition comprising:
   a) at least about 0.01% by weight, of a β-ketoester selected from the group consisting of 3,7-dimethyl-1,6-octadien-3-yl 3-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate-3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(β-naphthyl)-3-oxo-propionate, cis 3-hexen-1-yl 3-(β-naphthyl)-3-oxo-propionate, 9-decen-1-yl 3-(β-naphthyl)-3-oxo-propionate 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof; and
   b) from about 85% to about 99.99% by weight, of ingredients useful for formulating fabric softening compositions wherein component (b) comprises one or more ingredients selected from the group consisting of cationic fabric softening agents, nonionic fabric softening agents, liquid carrier, concentration aid, soil release agent, perfume, preservatives, stabilizers, and mixtures thereof.

2. A composition according to claim 1 comprising from about 0.2% to about 1% by weight, of said β-ketoester.

3. A composition according to claim 1 wherein component (b) comprises from about 1% to about 80%, by weight, of a cationic fabric softening agent.

4. A composition according to claim 1 wherein component (b) comprises:
   i) from about 5% to about 50% by weight, of a cationic fabric softening agent;
   ii) at least about 50% of a liquid carrier; and
   iii) optionally, from about 0 to about 15% by weight, of concentration aids.

5. A composition according to claim 4 wherein said cationic fabric softening agent is a quaternary ammonium compound having the formula:

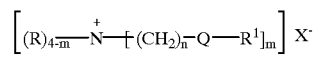

wherein Q has the formula:

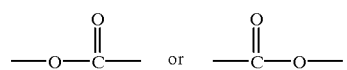

R is $C_1$–$C_6$ alkyl, $C_1$–$C_6$ hydroxyalkyl, benzyl, and mixtures thereof; each $R^1$ is independently linear or branched $C_{11}$–$C_{22}$ alkyl, linear or branched $C_{11}$–$C_{22}$ alkenyl, and mixtures thereof; X is any softener compatible anion; m is 2 or 3; n is 1 to 4.

6. A rinse added fabric softening composition comprising:
   a) at least about 0.01% by weight, of a β-ketoester having the formula:

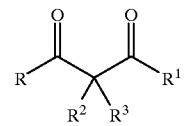

wherein R is selected from the group consisting of substituted or unsubstituted phenyl, substituted or unsubstituted benzyl, substituted or unsubstituted naphthyl, substituted or unsubstituted phenyl, substituted or unsubstituted nonanyl, substituted or unsubstituted heptyl, and mixtures thereof; $R^1$ is an alkoxy unit derived from a fragrance raw material alcohol selected from the group consisting, of 4-(1-methylethyl)cyclohexane-methanol, 2,4-dimethyl-3-cyclohexen-1-ylmethanol, (2,4-dimethylcyclohex-1-yl)methanol, (2,4,6-trimethyl-3-cyclohexen-1-yl) methanol, 2-phenylethanol, 1-(4-isopropylcyclohexyl)-ethanol, 2,2-dimethyl-3-(3-methylphenyl)propan-1-ol, 3-phenyl-2-propen-1-ol, 2-methyl-4-(2,2,3-trimethyl-3-cyclopenten-1-yl)-2-buten-1-ol, 3-methyl-5-phenylpentan-1-ol, 3-methyl-5-(2,2,3-trimethyl-3-cyclopenten-1-yl)-4-penten-2-ol, 2-methyl-4-phenylpentan-1-ol, cis-3-hexen-1-ol, 3,7-dimethyl-6-octen-1-ol, 3,7-dimethyl-2,6-octadien-1-ol, 7-methoxy-3,7-dimethyloctan-2-ol, 6,8-dimethylnonan-2-ol, cis-6-nonen-1-ol, 2,6-nonadien-1-ol, 4-methyl-3-decen-5-ol, benzyl alcohol, 2-methoxy-4-(1-propenyl)phenol, 2-methoxy-4-(2-propenyl)phenol, 3,7-dimethyl-octa-1,6-dien-3-ol, 2,6-dimethyl-octa-7-en-2-ol, and mixtures thereof,; $R^2$ and $R^3$ are each independently selected from the group consisting of hydrogen, $C_1$–$C_{20}$ substituted or unsubstituted linear alkyl, $C_3$–$C_{20}$ substituted or unsubstituted branched alkyl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; and
   b) from about 5% to about 99.99% by weight, of ingredients useful for formulating fabric softening compositions comprising:
   i) from about 5% to about 50% by weight, of a cationic fabric softening agent;
   ii) at least about 50% of a liquid carrier; and
   iii) optionally, from about 0 to about 15% by weight, of concentration aids.

7. A composition according to claim 6 wherein the β-ketoester pro-fragrance is selected from the group consisting of 3,7-dimethyl-1,6-octadien-3-yl 3-(β-naphthyl)-3-oxo-propionate, 2,6-dimethyl-7-octen-2-yl 3-(4- methoxyphenyl)-3-oxo-propionate, 2,6-dimethyl-7-octen-2-yl 3-(4-nitrophenyl)-3-oxo-propionate, 2,6-dimethyl-7-octen-2-yl 3-(,-naphthyl)-3-oxo-propionate, 3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2-dimethylpropionate, 3,7-dimethyl-1,6-octadien-3-yl 3-(β-naphthyl)-3-oxo-2-methylpropionate, 3,7-dimethyl-2,6-octadienyl 3-(,-naphthyl)-3-oxo-propionate, 3,7-dimethyl-2,6-octadienyl 3-heptyl-3-oxo-propionate, and mixtures thereof; and wherein the fabric softening agent is a quaternary ammonium compound having the formula:

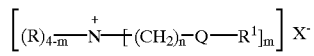

wherein Q has the formula:

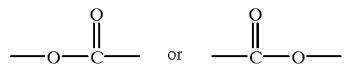

R is $C_1$–$C_6$ alkyl, $C_1$–$C_6$ hydroxyalkyl, benzyl, and mixtures thereof; each $R^1$ is independently linear or branched $C_{11}$–$C_{22}$ alkyl, linear or branched $C_{11}$–$C_{22}$ alkenyl, and mixtures thereof; X is any softener compatible anion; m is 2 or 3; n is 1 to 4.

8. A composition according to claim 1 comprising from about 0.01% to about 15% by weight, of said β-ketoester.

9. A composition according to claim 8 comprising from about 0.1% to about 10% by weight, of said β-ketoester.

10. A composition according to claim 1 wherein said fabric softening active is selected from the group consisting of:

i) an quaternary ammonium compound having the formula:

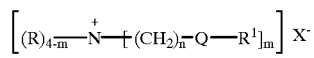

ii) a quaternary ammonium compound having the formula:

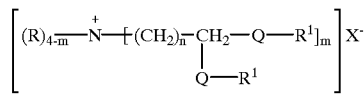

iii) and mixtures thereof;

wherein each R is independently $C_1$–$C_6$ alkyl, $C_1$–$C_6$ hydroxyalkyl, and mixtures thereof; $R^1$ is $C_{11}$–$C_{22}$ linear alkyl, $C_{11}$–$C_{22}$ branched alkyl, $C_{11}$–$C_{22}$ linear alkenyl, $C_{11}$–$C_{22}$ branched alkenyl, and mixtures thereof; Q is a carbonyl moiety independently selected from units having the formula:

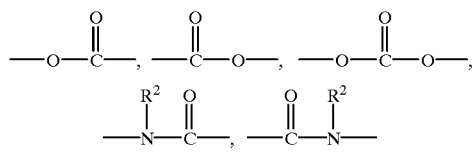

wherein $R^2$ is hydrogen, $C_1$–$C_4$ alkyl, $C_1$–$C_4$ hydroxyalkyl, and mixtures thereof; $R^3$ is hydrogen, $C_1$–$C_4$ alkyl, and mixtures thereof; X is selected from the group consisting of chloride, bromides methylsulfate, ethylsulfate, sulfate, nitrate, and mixtures thereof; the index m has the value from 1 to 4, the index n has the value from 1 to 4.

11. A composition according to claim 10 wherein Q has the formula:

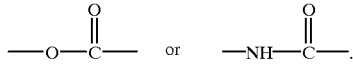

12. A composition according to claim 11 wherein the moiety —$O_2CR^1$ comprises an acyl unit, said acyl unit derived from a source of triglyceride selected from the group consisting of tallow, partially hydrogenated tallow, lard, partially hydrogenated lard, vegetable oils and/or partially hydrogenated vegetable oils, canola oil, safflower oil, peanut oil, sunflower oil, corn oil, soybean oil, tall oil, rice bran oil, and mixtures thereof.

13. A composition according to claim 10 wherein R is methyl, hydroxyalkyl, and mixtures thereof.

14. A composition according to claim 13 wherein n is equal to 2.

* * * * *